(12) United States Patent
Gumrukcu

(10) Patent No.: US 11,413,338 B2
(45) Date of Patent: Aug. 16, 2022

(54) METHODS AND COMPOSITIONS USING RECOMBINANT DENDRITIC CELLS FOR CANCER THERAPY

(71) Applicant: Enochian BioPharma, Inc., Los Angeles, CA (US)

(72) Inventor: Serhat Gumrukcu, Los Angeles, CA (US)

(73) Assignee: ENOCHIAN BIOPHARMA, INC., Los Angeles, CA (US)

( * ) Notice: Subject to any disclaimer, the term of this patent is extended or adjusted under 35 U.S.C. 154(b) by 313 days.

(21) Appl. No.: 16/511,413

(22) Filed: Jul. 15, 2019

(65) Prior Publication Data

US 2020/0016250 A1      Jan. 16, 2020

Related U.S. Application Data

(60) Provisional application No. 62/698,254, filed on Jul. 15, 2018.

(51) Int. Cl.

| | | |
|---|---|---|
| *A61K 39/00* | (2006.01) | |
| *A61K 39/12* | (2006.01) | |
| *A61K 35/15* | (2015.01) | |
| *C07K 14/52* | (2006.01) | |
| *C07K 14/705* | (2006.01) | |
| *A61P 35/00* | (2006.01) | |

(52) U.S. Cl.
CPC .......... *A61K 39/0011* (2013.01); *A61K 35/15* (2013.01); *A61K 39/12* (2013.01); *A61P 35/00* (2018.01); *C07K 14/521* (2013.01); *C07K 14/70578* (2013.01); *C07K 14/70596* (2013.01); *A61K 2039/5154* (2013.01)

(58) Field of Classification Search
CPC ................................................ A61K 39/0011
See application file for complete search history.

(56) References Cited

U.S. PATENT DOCUMENTS

| | | | |
|---|---|---|---|
| 6,268,138 | B1 | 7/2001 | Dalla-Favera et al. |
| 7,615,529 | B2 | 11/2009 | Kong-Beltran et al. |
| 7,723,107 | B2 | 5/2010 | Kirkin et al. |
| 7,771,998 | B2 | 8/2010 | Kirkin et al. |
| 9,234,175 | B2 | 1/2016 | Mule |
| 9,347,044 | B2 | 5/2016 | Brown et al. |
| 9,914,783 | B1 | 3/2018 | Afar et al. |
| 10,272,111 | B2 | 4/2019 | Stripecke et al. |
| 2003/0202963 | A1 | 10/2003 | Crystal et al. |
| 2009/0029457 | A1* | 1/2009 | Kirkin ............... A61P 35/00 435/325 |
| 2012/0148577 | A1 | 6/2012 | Fuchs et al. |
| 2012/0201794 | A1 | 8/2012 | Chen et al. |
| 2012/0244181 | A1* | 9/2012 | Mule ............... A61P 35/00 424/204.1 |
| 2012/0258126 | A1 | 10/2012 | Scholler et al. |
| 2015/0337042 | A1 | 11/2015 | Reilly et al. |
| 2018/0000899 | A1 | 1/2018 | Francois et al. |

FOREIGN PATENT DOCUMENTS

| | | | |
|---|---|---|---|
| EP | 1809737 B1 | 11/2010 | |
| EP | 1794327 A4 | 2/2011 | |
| EP | 1658097 B1 | 6/2011 | |
| EP | 2201100 B1 | 3/2016 | |
| EP | 1882031 B1 | 11/2017 | |
| WO | 2008055354 A1 | 5/2008 | |
| WO | WO2008/055354 | * 5/2008 | ............... C12N 5/10 |
| WO | 2009149539 A1 | 12/2009 | |

OTHER PUBLICATIONS

Magni, Michele et al., "Induction of Cyclophosphamide-Resistance by Aldehyde-Dehydrogenase Gene Transfer", Blood, 87(3): 1097-1103 (1996).

International Search Report dated Oct. 17, 2019 received in PCT Application No. PCT/US2019/041786.

Bohlson, et al., "CD93 Is Rapidly Shed from the Surface of Human Myeloid Cells and the Soluble Form Is Detected in Human Plasma" J. Immunol. (2005) 175: 1239-1247.

Kuo, et al., Site-Specific Gene Editing of Human Hematopoietic Stem Cells for X-Linked Hyper-IgM Syndrome. Cell Report (2018) vol. 23, No. 9, 2606-2616.

Bonehill, et al., "Enhancing the T-cell Stimulatory Capacity of Human Dendritic Cells by Co-electroporation With CD40L, CD70 and Constitutively Active TLR4 Encoding mRNA", The American Society of Gene Therapy (2008) vol. 16, No. 6, pp. 117-1180.

Chen, et al., "Extronadol induction of therapeutic immunity in the tumor mocroenvironment after intratumoral delivery of Tbet gene-modified dendritic cells", Cancer Gene Therapy (2013) 20, 469-477.

Vissers, et al., "BLC CXCL13) is expressed by different dendritic cell subsets in vitro and in vivo", Eur. J. Immunol. (2001) 31: 1544-1549.

Eriksson, et al., "Activation of myeloid and endothelial cells by CD40L gene therapy supports T-cell expansion and migration into the tumor microenvimnment". Gene Therapy (2017) 24, 92-103.

Miller, et al., "The Journey from Discoveries in Fundamental Immunology to Cancer Immunotherapy", Cancer Cell (2015) 27; 439-449.

Thurner, et al., "Vaccination with Mage-3A1 Peptide-pulsed Mature, Monocyte-derived Dendritic Cells Expands Specific Cytotoxic T Cells and Induces Regression of Some Metastases in Advanced Stage IV Melanoma", J. Ex. Med. (1999) vol. 190, No. 11, pp. 1669-1678.

(Continued)

*Primary Examiner* — Scott Long
(74) *Attorney, Agent, or Firm* — Troutman Pepper Hamilton Sanders LLP

(57) ABSTRACT

Disclosed herein are methods and compositions for treating cancer by eliciting an immune response by administering dendritic cells expressing heterologous proteins. In some embodiments, a dendritic cell comprises one or more heterologous nucleic acid molecules encoding for CD40L and CXCL13. In some embodiments, the dendritic cell further comprises a heterologous nucleic acid molecule encoding for CD93. In yet additional embodiments, the dendritic cells expressing heterologous proteins are activated.

20 Claims, 18 Drawing Sheets

Specification includes a Sequence Listing.

(56) References Cited

OTHER PUBLICATIONS

Sallusto et al, ",Dendritic Cells Use Macropinocytosis and the Mannose Receptor to Concentrate Macromolecules in the Major Histocompatibility Comples Class II Compartment: Downregulations by Cytokines and Bacterial Products" (1995) J. Exp. Med. v. 182, pp. 389-400.
Nestle et al., "Vaccination of melanoma patients with peptide- or tumor lysate-pulsed deendritic cells", Nature Medicine (1998) vol. 4, No. c 3, pp. 328-332.
Scanlan, et al., "Cancer/testis antigens: an expanding family of targets for cancer immunotherapy", Immunological Reviews (2002) vol. 188: pp. 22-32.
Iriguchi, et al., "Toward the development of tru "off-the-shelf" symthetic T-cell immunotherapy", Cancer Science (2018) 110: pp. 16-22.
Marchesi, et al., "CXCL13 expression in the gut promotes accumulation of IL-22-producing lymphoid tissue-inducer cells, and formation of isolated lymphoid follicles". Nture Publishing Group (2009) vol. 2; No. 6, pp. 486-494.
Weon, et al., "The MAGE protein family and cancer" Cell Biology (2015) 37: pp. 1-8.
Zhong et al., "Recombinant adenovirus is an efficient and non-perturbing genetic vector for human dendritic cells", Eur. J. Immunol. 1999) 29: pp. 964-972.

\* cited by examiner

SEQUENCE LISTING

```
<160> NUMBER OF SEQ ID NOS: 6

<210> SEQ ID NO 1
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggttg gacaagatag aagatgaaag gaatcttcat     180
gaagattttg tattcatgaa aacgatacag agatgcaaca caggagaaag atccttatcc     240
ttactgaact gtgaggagat taaaagccag tttgaaggct ttgtgaagga tataatgtta     300 aacaagagg agacgaagaa agaaaacagc tttgaaatgc aaaaaggtga tcagaatcct     360
caaattgcgg cacatgtcat aagtgaggcc agcagtaaaa caacatctgt gttacagtgg     420
```

```
gctgaaaaag gatactacac catgagcaac aacttggtaa ccctggaaaa tgggaaacag      480
ctgaccgtta aaagacaagg actctattat atctatgccc aagtcacctt ctgttccaat      540
cgggaagctt cgagtcaagc tccatttata gccagcctct gcctaaagtc ccccggtaga      600
ttcgagagaa tcttactcag agctgcaaat acccacagtt ccgccaaacc ttgcgggcaa      660
caatccattc acttgggagg agtatttgaa ttgcaaccag gtgcttcggt gtttgtcaat      720
gtgactgatc aagccaagt gagccatggc actggcttca cgtcctttgg cttactcaaa       780
ctc                                                                    783

<210> SEQ ID NO 2
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgaagttca tctcgacatc tctgcttctc atgctgctgg tcagcagcct ctctccagtc      60
caaggtgttc tggaggtcta ttacacaagc ttgaggtgta gatgtgtcca agagagctca     120
gtctttatcc ctagacgctt cattgatcga attcaaatct gccccgtgg aatggttgt       180 ccaagaaaag aaatcatagt ctggaagaag aacaagtcaa ttgtgtgtgt ggaccctcaa     240
gctgaatgga tacaaagaat gatggaagta ttgagaaaaa gaagttcttc aactctacca     300
gttccagtgt ttaagagaaa gattccc                                         327

<210> SEQ ID NO 3
<211> LENGTH: 1956
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggccacct ccatgggcct gctgctgctg ctgctgctgc tcctgaccca gcccggggcg      60
gggacgggag ctgacacgga ggcggtggtc tgcgtgggga ccgcctgcta cacggcccac     120
tcgggcaagc tgagcgctgc cgaggcccag aaccactgca accagaacgg ggcaacctg      180 gccactgtga agagcaagga ggaggcccag cacgtccagc gagtactggc ccagctcctg     240
aggcgggagg cagccctgac ggcgaggatg agcaagttct ggattgggct ccagcgagag     300
aagggcaagt gcctggaccc tagtctgccg ctgaagggct tcagctgggt gggcggggg      360 gaggacacgc cttactctaa ctggcacaag gagctccgga actcgtgcat ctccaagcgc     420
tgtgtgtctc tgctgctgga cctgtcccag ccgctccttc cagccgcct ccccaagtgg      480 tctgagggcc cctgtgggag cccaggctcc cccggaagta acattgaggg cttcgtgtgc     540
aagttcagct tcaaaggcat gtgccggcct ctggccctgg ggggcccagg tcaggtgacc     600
tacaccaccc ccttccagac caccagttcc tccttggagg ctgtgcccct tgcctctgcg     660
gccaatgtag cctgtgggga aggtgacaag gacgagactc agagtcatta tttcctgtgc     720
aaggagaagg cccccgatgt gttcgactgg ggcagctcgg gccccctctg tgtcagcccc     780
aagtatggct gcaacttcaa caatgggggc tgccaccagg actgctttga aggggggat      840 ggctccttcc tctgcggctg ccgaccagga ttccggctgc tggatgacct ggtgacctgt     900
```

```
gcctctcgaa acccttgcag ctccagccca tgtcgtgggg gggccacgtg cgtcctggga      960
ccccatggga aaaactacac gtgccgctgc ccccaagggt accagctgga ctcgagtcag     1020
ctggactgtg tggacgtgga tgaatgccag gactccccct gtgcccagga gtgtgtcaac     1080
acccctgggg gcttccgctg cgaatgctgg gttggctatg agccgggcgg tcctggagag     1140
ggggcctgtc aggatgtgga tgagtgtgct ctgggtcgct cgccttgcgc ccagggctgc     1200
accaacacag atggctcatt tcactgctcc tgtgaggagg ctacgtcct ggccggggag      1260 gacgggactc agtgccagga cgtggatgag tgtgtgggcc cggggggccc cctctgcgac     1320
agcttgtgct tcaacacaca agggtccttc cactgtggct gcctgccagg ctgggtgctg     1380
gccccaaatg gggtctcttg caccatgggg cctgtgtctc tgggaccacc atctgggccc     1440
cccgatgagg aggacaaagg agagaaagaa gggagcaccg tgccccgtgc tgcaacagcc     1500
agtcccacaa ggggccccga gggcaccccc aaggctacac ccaccacaag tagaccttcg     1560
ctgtcatctg acgccccat cacatctgcc ccactcaaga tgctggcccc cagtgggtcc      1620
ccaggcgtct ggagggagcc cagcatccat acgccacag ctgcctctgg cccccaggag      1680
cctgcaggtg gggactcctc cgtggccaca caaaacaacg atggcactga cgggcaaaag     1740 ctgctttat tctacatcct aggcaccgtg gtggccatcc tactcctgct ggccctggct      1800
ctggggctac tggtctatcg caagcggaga gcgaagaggg aggagaagaa ggagaagaag     1860
ccccagaatg cggcagacag ttactcctgg gttccagagc gagctgagag cagggccatg     1920
gagaaccagt acagtccgac acctgggaca gactgc                               1956
```

<210> SEQ ID NO 4
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

```
Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
            35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
                100                 105

<210> SEQ ID NO 6
<211> LENGTH: 652
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Thr Ser Met Gly Leu Leu Leu Leu Leu Leu Leu Leu Leu Thr
1               5                   10                  15

Gln Pro Gly Ala Gly Thr Gly Ala Asp Thr Glu Ala Val Val Cys Val
                20                  25                  30

Gly Thr Ala Cys Tyr Thr Ala His Ser Gly Lys Leu Ser Ala Ala Glu
            35                  40                  45

Ala Gln Asn His Cys Asn Gln Asn Gly Gly Asn Leu Ala Thr Val Lys
        50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95
```

-continued

```
Leu Gln Arg Glu Lys Gly Lys Cys Leu Asp Pro Ser Leu Pro Leu Lys
            100                 105                 110

Gly Phe Ser Trp Val Gly Gly Glu Asp Thr Pro Tyr Ser Asn Trp
        115                 120                 125

His Lys Glu Leu Arg Asn Ser Cys Ile Ser Lys Arg Cys Val Ser Leu
        130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
        195                 200                 205

Ser Ser Ser Leu Glu Ala Val Pro Phe Ala Ser Ala Ala Asn Val Ala
    210                 215                 220

Cys Gly Glu Gly Asp Lys Asp Glu Thr Gln Ser His Tyr Phe Leu Cys
225                 230                 235                 240

Lys Glu Lys Ala Pro Asp Val Phe Asp Trp Gly Ser Ser Gly Pro Leu
                245                 250                 255

Cys Val Ser Pro Lys Tyr Gly Cys Asn Phe Asn Asn Gly Gly Cys His
            260                 265                 270

Gln Asp Cys Phe Glu Gly Gly Asp Gly Ser Phe Leu Cys Gly Cys Arg
        275                 280                 285

Pro Gly Phe Arg Leu Leu Asp Asp Leu Val Thr Cys Ala Ser Arg Asn
    290                 295                 300

Pro Cys Ser Ser Ser Pro Cys Arg Gly Gly Ala Thr Cys Val Leu Gly
305                 310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
        355                 360                 365

Cys Trp Val Gly Tyr Glu Pro Gly Gly Pro Gly Glu Gly Ala Cys Gln
    370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
            420                 425                 430

Gly Pro Gly Gly Pro Leu Cys Asp Ser Leu Cys Phe Asn Thr Gln Gly
        435                 440                 445

Ser Phe His Cys Gly Cys Leu Pro Gly Trp Val Leu Ala Pro Asn Gly
    450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
            500                 505                 510
```

```
                    -continued
Thr Pro Thr Thr Ser Arg Pro Ser Leu Ser Ser Asp Ala Pro Ile Thr
        515                 520                 525

Ser Ala Pro Leu Lys Met Leu Ala Pro Ser Gly Ser Pro Gly Val Trp
    530                 535                 540

Arg Glu Pro Ser Ile His His Ala Thr Ala Ala Ser Gly Pro Gln Glu
545                     550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Leu Ala Leu Ala Leu Gly Leu Leu Val Tyr Arg Lys
        595                 600                 605

Arg Arg Ala Lys Arg Glu Glu Lys Lys Glu Lys Lys Pro Gln Asn Ala
        610                 615                 620

Ala Asp Ser Tyr Ser Trp Val Pro Glu Arg Ala Glu Ser Arg Ala Met
625                     630                 635                 640

Glu Asn Gln Tyr Ser Pro Thr Pro Gly Thr Asp Cys
                645                 650
```

METHODS AND COMPOSITIONS USING RECOMBINANT DENDRITIC CELLS FOR CANCER THERAPY

CLAIM OF PRIORITY

This application claims priority to U.S. Provisional Application No. 62/698,254, filed Jul. 15, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 3, 2019, is named 146616_00302_SL.txt and is 14,051 bytes in size.

BACKGROUND

Cancer therapies encompass a wide range of therapeutic approaches, including surgical, radiation, chemotherapy, as well as cell-based immunotherapy. While these various therapeutic approaches provide a broad selection of treatments, existing therapeutics suffer from many disadvantages, including a lack of selectivity of targeting cells over healthy cells, toxicity, and resistance by the cancer to the treatment. More recent approaches utilizing targeted therapeutics that interfere with key cellular processes of cancer cells preferentially over normal cells, have led to chemotherapeutic regimens with fewer side effects as compared to non-targeted therapies such as radiation treatment.

Cancer immunotherapy has also emerged as a promising therapeutic approach to augment and complement existing standards of care. See, e,g, Miller et al. Cancer Cell; 27:439-449 (2015). These approaches include utilizing antibody to modulate the immune system to kill cancer cells. Anti-tumor immune responses in some patients with solid tumors have been enhanced by anti-PD1 treatment. However, only a fraction of patients are responsive to such treatment, highlighting the need for additional approaches and further cancer treatments to augment and complement existing therapeutic standards of care.

SUMMARY

Provided herein are dendritic cells comprising one or more heterologous nucleic acid molecules encoding for CD40L and/or CXCL13.

In some embodiments, the one or more heterologous nucleic acid molecules encodes for CD93.

Further provided herein is a dendritic cell comprising a heterologous CD40L protein and a heterologous CXCL13 protein.

In some embodiments, the cell further comprises a heterologous CD93 protein.

Further provided herein are antigen activated dendritic cells, wherein the dendritic cell comprises one or more heterologous nucleic acid molecules encoding for CD40L and/or CXCL13. In some embodiments, the one or more heterologous nucleic acid molecules encodes for CD93.

In some embodiments, the antigen activated dendritic cell is activated by exposure to one or more antigens.

In some embodiments, the antigen is a tumor antigen.
In some embodiments, the antigen is a viral antigen.
In some embodiments, the antigen is a cell lysate.

In some embodiments, the cell lysate is allogeneic or autologous to the antigen activated dendritic cell.

In some embodiments, the cell lysate is a lysate comprising one, or a combination of allogeneic melanoma cell lysates.

In some embodiments, the allogeneic melanoma cell lysate is a DDM-1.7 cell lysate, a DDM-1.13 cell lysate, or a combination thereof.

In some embodiments, the cell lysate is a whole cell lysate.

In some embodiments, the cell lysate is a tumor cell lysate.

Further provided herein is a composition of comprising a cell described herein (recombinant dendritic cell or activated cell, or related composition), wherein the composition does not comprise a heterologous antigen.

Further provided herein is a pharmaceutical composition comprising cells provided herein.

Further provided herein are methods of treating a solid tumor, cancer, or malignancy in a subject comprising administering to the subject any of cells or compositions provided for herein.

Further provided herein are methods of treating a solid tumor, cancer, or malignancy in a subject comprising administering to the subject any of cells or compositions provided for herein.

In some embodiments, the method further comprises:
screening a protein expression profile of a resected tumor or biopsy sample from the subject to cross-match a protein expression profile of an allogeneic tumor lysate prior to administration; and
administering an allogeneic tumor lysate activated dendritic cell or activated dendritic cell composition if at least three fragments of the protein expression profile of the resected tumor or biopsy sample cross-match the protein expression profile of the allogeneic tumor lysate.

In some embodiments, the allogeneic tumor lysate is derived from an allogeneic melanoma cell line selected from the group consisting of DDM-1.7, DDM-1.13, or a combination thereof.

In some embodiments, the dendritic cell does not have the same HLA type as the subject.

In some embodiments, the cancer is a solid tumor selected from the group consisting of fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma/colorectal cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In some embodiments, the route of administration is via intratumoral, peritumoral, intradermal, subcutaneous, intramuscular, intraperitoneal, injection.

In some embodiments, the administering is via subcutaneous, intratumoral or intradermal injection.

In some embodiments, the dendritic cell or composition is frozen or cryopreserved and thawed prior to administration.

In some embodiments, the dendritic cell is not pulsed with an antigen prior to administration.

Further provided herein is a kit comprising any of the dendritic cells or compositions provided for herein. In some embodiments, the dendritic cells or compositions are frozen or cryopreserved in a container, and optionally comprising a frozen or cryopreserved allogeneic tumor lysate in a separate container.

Further provided herein is a kit comprising any of the dendritic cells or compositions described herein, wherein the dendritic cell or composition is frozen or cryopreserved in a container, and optionally comprising a frozen or cryopreserved autologous tumor lysate in a separate container.

Further provided herein is a kit comprising any of the dendritic cells or compositions described herein wherein the activated dendritic cell or composition is frozen or cryopreserved in a container.

In some embodiments, the kit further comprises separate containers comprising one or more buffers, and optionally comprising one or more activation agents.

In some embodiments, the kit further comprises instructions for incubating and/or processing the dendritic cells or compositions.

Further provided herein is a method of treating cancer in a subject comprising:
  screening a protein expression profile of resected tumor or biopsy samples from the subject to cross-match a protein expression profile of an allogeneic tumor lysate prior to administration;
  if at least three fragments of the protein expression profile of resected tumor or biopsy samples match with the protein expression profile of the allogeneic tumor lysate, administering to the subject any of the dendritic cells or compositions of provided for herein; or
  if the at least three fragments of the protein expression profile of resected tumor or biopsy samples do not match the allogeneic tumor lysate protein expression profile, then
    (a) administering to the subject a composition comprising an autologous tumor lysate pulsed with any of the dendritic cells or compositions described herein or
    (b) administering to the subject any of the cells or compositions described herein, which has not been pulsed with an antigen.

Further provided herein is a method of treating cancer in a subject comprising administering to the subject any of the dendritic cells or compositions of as provided for herein, wherein the dendritic cell or composition has not been pulsed with a tumor antigen.

Further provided herein is a method of treating cancer in a subject comprising administering to the subject any of the dendritic cells or compositions as provided for herein, wherein the dendritic cell has been pulsed with a tumor antigen or lysate.

Further provided herein is a method of activating the immune system, comprising administering to a subject in need thereof an effective amount of any of the dendritic cells or compositions described herein.

Further provided herein is a method of producing immature dendritic cells comprising:
  culturing CD14+ and/or CD1a+ monocytes heterologously expressing CD40L, CXCL13, and optionally CD93 into immature dendritic cells in vitro.

In some embodiments, the method comprises contacting the immature dendritic with a composition comprising one or more of: TNF-α, IFN-α, IFN-γ, and pIC.

In some embodiments, the method further comprises producing the CD14+ monocytes heterologously expressing CD40L, CXCL13, and optionally CD93.

In some embodiments, the producing comprises contacting CD14+ monocytes with one or more vectors encoding for CD40L, CXCL13, and optionally CD93.

In some embodiments, the vector is a recombinant adenoviral vector, a recombinant retroviral vector, or a recombinant lentiviral vector, or a combination thereof.

In some embodiments, the producing the CD14+ monocytes heterologously expressing CD40L, CXCL13, and optionally CD93 comprises contacting the monocytes with one or more CRISPR constructs that produces CD14+ monocytes heterologously expressing CD40L, CXCL13, and optionally CD93.

In some embodiments, the CRISPR construct is CAS9.

In some embodiments, the contacting comprises transfection, transduction, electroporation, infection, or any combination thereof.

In some embodiments, the method further comprises freezing the immature dendritic cells.

In some embodiments, the method further comprises contacting the immature dendritic cells with an autologous tumor lysate or allogeneic tumor lysate before maturation.

In some embodiments, the method further comprises freezing the dendritic cells after maturation.

In some embodiments, the CD14+ monocytes are further modified to heterologously express CD93.

In some embodiments, the allogeneic tumor lysate is derived from an allogeneic melanoma cell line selected from the group consisting of DDM-1.7, DDM-1.13, or a combination thereof.

In some embodiments, the lysate is a whole cell lysate.

In some embodiments, graft versus tumor (GVT) response is increased in the patient.

In some embodiments, at a time-frame of from 4-14 days following administration of the dendritic cells or compositions, the patient is further administered an immune checkpoint inhibitor, including any one or combination of two check point inhibitors, including an inhibitor of PD-1 or PD-L1 (B7-H1), such as an anti-PD-1 antibody, including nivolumab (Nivolumab from Bristol-Myers Squibb), pembrolizumab/lambrolizumab, also known as MK-3475 (Keytruda from Merck), pidilizumab (Curetech), AMP-224 (Amplimmune), or an anti-PD-L1 antibody, including MPDL3280A (Roche), MDX-1105 (Bristol Myer Squibb), MEDI-4736 (AstraZeneca) and MSB-0010718 C (Merck), an antagonist of CTLA-4, such as an anti-CTLA-4 antibody including anti-CTLA4 antibody Yervoy™ (ipilimumab, Bristol-Myers Squibb), tremelimumab (Pfizer), Ticilimumab (AstraZeneca) or AMGP-224 (Glaxo Smith Kline), or a tumor specific antibody trastuzumab (Herceptin) for breast cancer, rituximab (Rituxan) for lymphoma, or cetuximab (Erbitux).

In some embodiments, the method further comprises administering one or more additional agents commonly used to treat cancer.

In some embodiments, the additional agent is selected from radiation, chemotherapy, an antibody drug conjugate, and an immune modulating antibody.

In some embodiments, the chemotherapy is of cisplatin, carboplatin, paclitaxel, docetaxel, gemcitabine, vinorelbine, vinblastine, irinotecan, etoposide, or pemetrexed, or combinations thereof, or a pharmaceutically acceptable salt thereof.

In some embodiments, the immune modulating antibody is an anti-PD-1 antibody, an anti-PD-L1 antibody, an anti-CD40 antibody, an anti-CTLA-4 antibody, or an anti-OX40 antibody, or any combination thereof.

In some embodiments, the antibody drug conjugate targets c-Met kinase, LRRC15, EGFR, or CS1, or any combination thereof.

In some embodiments, the treatment or increasing the immune response is repeated periodically for time frames of from once every 5 days, once every week, once every 10 days, once every 14 days, once every 21 days, once every month, to once every two months, to once every 3 months, to once every 4 months, to once every 5 months, to once every 6 months, or once every 7 months, or once every 8 months, or once every 9 months, or once every 10 months, or once every 11 months, or once annually as a maintenance treatment for as long as the patient exhibits improvement, or stable/non-progressing disease.

Disclosed herein are methods and compositions for treating cancer by eliciting an immune response by administering dendritic cells expressing heterologous proteins. In some embodiments, a dendritic cell comprises one or more heterologous nucleic acid molecules encoding for CD40L and CXCL13. In some embodiments, the dendritic cell further comprises a heterologous nucleic acid molecule encoding for CD93. In further embodiments, a dendritic cell comprises one or more heterologous nucleic acid molecules encoding for CD40L and CD93. In further embodiments, a dendritic cell comprises one or more heterologous nucleic acid molecules encoding for CXCL13 and CD93.

In some embodiments, a dendritic cell overexpressing CD40L and CXCL13, and optionally CD93 may be an antigen activated dendritic cell. In some embodiments, the antigen may be a tumor antigen or a viral antigen. In some embodiments, the dendritic cells are allogenic or autologous to the subject.

In further embodiments, a method of treating cancer in a subject comprises administering to the subject a composition comprising a dendritic cell, wherein the dendritic cell overexpresses one or more proteins selected from CD40L, CXCL13, and CD93. In some embodiments, the method further comprises:
(a) obtaining a protein expression profile of a resected tumor or biopsy sample from the subject;
(b) comparing the protein expression profile of the resected tumor or biopsy sample to the protein expression profile of a melanoma cell lysate; and
(c) if at least three markers in the protein expression profile of the resected tumor or biopsy sample match with the protein expression profile of the melanoma cell lysate, then co-culturing the dendritic cell with the melanoma cell lysate to activate the dendritic cell, and administering to the subject a composition comprising the activated dendritic cell; or
(d) if at least three markers in the protein expression profile of the resected tumor or biopsy sample do not match with the protein expression profile of the melanoma cell lysate, then co-culturing the dendritic cell with the autologous tumor or biopsy lysate to activate the dendritic cell, and administering to the subject a composition comprising the autologously activated dendritic cell.

In an additional embodiment, a method of producing immature dendritic cells comprises:
(a) isolating CD14+ monocytes from a subject;
(b) overexpressing CD40L, CXCL13, and CD93 in the isolated CD14+ monocytes; and
(c) differentiating the CD14+ monocytes into immature dendritic cells in vitro.

BRIEF DESCRIPTION OF THE DRAWINGS

FIG. 1A is a diagram showing the mechanism of action of CD40L expression. FIG. 1B is a diagram showing the immune recruitment process of CXCL13 expression. FIG. 1C is a schematic showing cancer-immunity cycle. FIG. 1D is a schematic showing various stages of dendritic cell maturation.

DETAILED DESCRIPTION

Figure 1A:
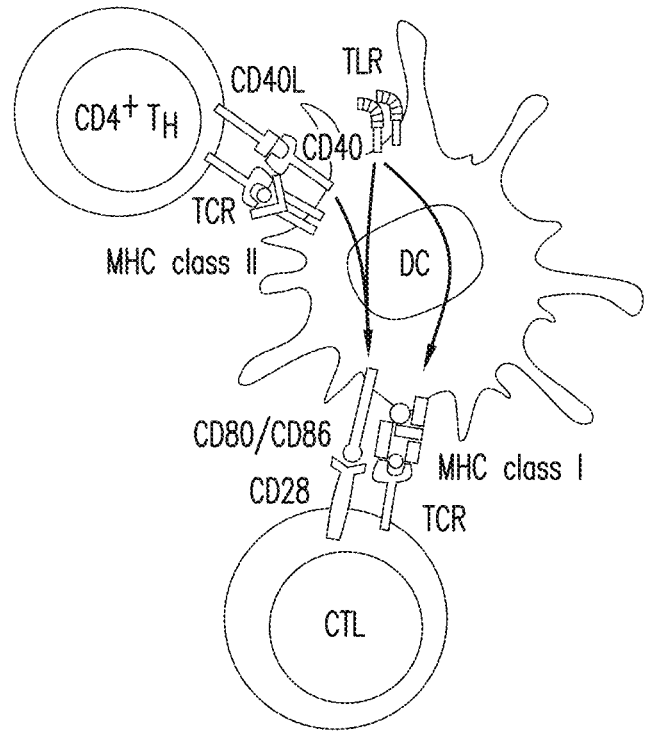
FIGS. 1A-D are diagrams and schematics showing various expression and activation processes in certain immune cells.
Figure 1B:
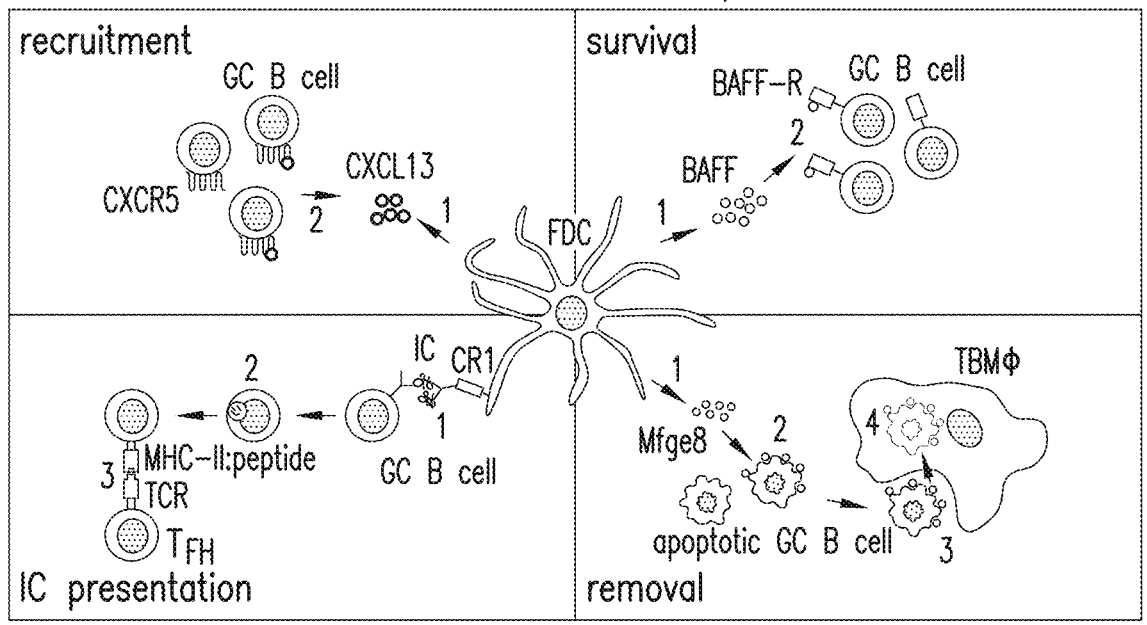

The present embodiments are directed, in part, to methods and compositions relating to dendritic cells transduced with CD40L, CXCL13, and/or CD93. The CD40L, CXCL13, and/or CD93 can be human. In some embodiments, the CD40L, CXCL13, and/or CD93 is rodent (mouse or rat) or pig. The cells comprising the heterologously expressed proteins can be referred to as recombinant cells. The compositions can be a stand-alone recombinant DC (dendritic cell) composition, or in alternative embodiments the recombinant DC cells can be antigen activated by contacting the cells, which can also be referred to as "loading," with tumor lysate, or alternatively, loaded with allogeneic ("off the shelf") tumor lysate as a vaccination and/or immune adjuvant for subjects with solid tumors and malignancies. In some embodiments, the tumor lysate is allogeneic in reference to the source of the dendritic cells. In some embodiments, the tumor lysate is autologous in reference to the source of the dendritic cells.

Dendritic cells (DCs) are professional antigen processing cells. They have a number of receptors that enhance the uptake of antigens, and they are specialized to convert these antigens into MHC-peptide complexes that can be recognized by lymphocytes.

While not wishing to be bound by theory, the present compositions and methods are based at least in part on the ability of recombinant (or transgenic) dendritic cells to build a mixed leukocyte reaction (MLR) at the injection site. When tested in a well-known clinical assay-MLR, recombinant alloDCs as described herein, were the major stimulators and were unusually potent. In some embodiments, the DCs can be allogeneic to the subject. In such embodiments, the DCs can be referred to as alloDCs. alloDCs are cells that are allogeneic as compared to the subject that they are being administered to.

In some embodiments, the DCs are transduced with CD40L and/or CXCL13 in order to maximize the attraction of patients' T cells and B cells, and generate the cascade of anti-tumor cellular and humoral immune response. In some embodiments, the DCs are transduced with CD40L and CXCL13. In some embodiments, the DCs are transduced with CD40L, CXCL13, and CD93. In some embodiments, the DCs are transduced with CD40L and CD93. In some embodiments, the DCs are transduced with CXCL13 and CD93. In some embodiments, the cells are not transduced with CD93. In some embodiments, the DCs do not heterologously express CD93.

In optional further embodiments, transduction of the CD40L+ and CXCL13+ alloDCs with CD93 facilitates the cross-talk between the allogeneic DCs and the host DCs, creating a stable and sustained host anti-tumor immunogenicity.

In some embodiments, human CD14+ monocytes are transfected with a recombinant vector encoding for CD40L and CXCL13 (and optionally CD93), or any, combination thereof as described herein, to be stably expressed on the human monocytes. Positively transduced monocytes can be selected and the monocytes can then be differentiated into immature and/or mature DCs in vitro. For the resected and biopsied malignant patients, the autologous tumor lysate can be generated and the tumor lysate can be presented to the immature recombinant alloDCs (recombinant im alloDcs) for the autologous tumor lysate to be processed by the recombinant im alloDcs. In some embodiments, the protein expression profile of the resected tumor samples and biopsy samples are screened. If the expression profiling indicates at least 3 fragments shared with GMP-MCV, then the recombinant imDC are loaded with GMP-MCV before the DCs are matured in vitro. For any non-resectable and non-biopsyable patient, the recombinant CD40L+CXCL13+ alloDC (or optionally further including CD93+) can be administered to the patient without antigen loading as an immune adjuvant. Using this CD40L+CXCL13+(optional) CD93 AlloDC approach, late stage cancer patients can mount new antitumor cellular and humoral immune response to tumor antigens and, without being bound to any particular mechanism, enhance the immune response.

Another tumor lysate that could be used to activate the recombinant DCs, includes DDM-1.7 and/or DDM-1.13. A description of DDM-1.7 and DDM-1.13 can be found in U.S. Pat. Nos. 7,771,998 and 7,723,107 (including the publicly available deposit information: ECACC 01112339 and ECACC 01112338, respectively), each of which are hereby incorporated by reference in its entirety.

As used herein, dendritic cells that are immature are those having the following marker characteristics: CD1a positive, CD14 negative, and CD83 negative/low.

In some embodiments, the source of dendritic cells can be from donor peripheral blood, and includes dendritic cells derived from CD14+ monocytes or CD34+ cells. In some embodiments, the donor is not the same as the subject being treated with the dendritic cells and compositions described herein.

In recent years it has been realized that an efficient manner of antigen delivery to T cells, especially to naive T cells, is by way of dendritic cells. Dendritic cells (DC) are the most efficient antigen presenting cells and DC based immunotherapy have already been used in different settings for treatment of cancer ((Kugler et al., 2000, Nat. Med., v. 6, pp. 332-336; Nestle et al., 1998, Nature (Med.), v. 4, pp. 328-332; Thurner et al., 1999, J. Exp. Med., v. 190, pp. 1669-1678)) demonstrating high potency of this way of immunization.

One of the unique properties of DCs is their ability to uptake exogenous proteins by endocytosis, which are then processed and presented as peptide epitopes on their surface in conjunction with MHC class I antigens. The antigen presenting dendritic cells can be recognized by cytotoxic T cells. This property is important when tumor cell antigens are applied in form of tumor lysates or apoptotic bodies added exogenously. High endocytic activity is believed to be associated with the immature state of DC differentiation based on comparison of immature and mature DC (Sallusto et al., 1995, J. Exp. Med., v. 182, pp. 389-400).

In some embodiments, the recombinant dendritic cells are treated with interferon-alpha (IFN-α) and/or 5'-aza-2'deoxycytidine (Aza) before or during loading the recombinant dendritic cells with tumor cell lysate/and or antigen. See, https://doi.org/10.1101/531616.

In some embodiments, purified human CD14+ monocytes are transduced with a recombinant vector, such as an adenoviral or lentiviral vector, comprising human CD40L and CXCL13, and optionally also CD93 constructs, allowing the recombinant molecules to be expressed on purified human monocytes. Positively transduced monocytes are then selected and these are then differentiated into immature DCs (imDC) in vitro, and are referred to a recombinant allogeneic DCs (recombinant alloDCs). In some embodiments, the expression is stable expression. In some embodiments, the expression is over-expression. "Over-expression" refers to a level that is at least 10%, 20%, 30%, 40%, 50%, 60%, 70%, 80%, 90%, 100%, 200%, 300%, 400%, or 500% over native expression levels. Native expression levels refer to expression levels of the cells that have not been transduced with a vector to express the heterologous protein or proteins of interest, such as CD40L, CXCL13, and/or CD93.

Figure 1C:
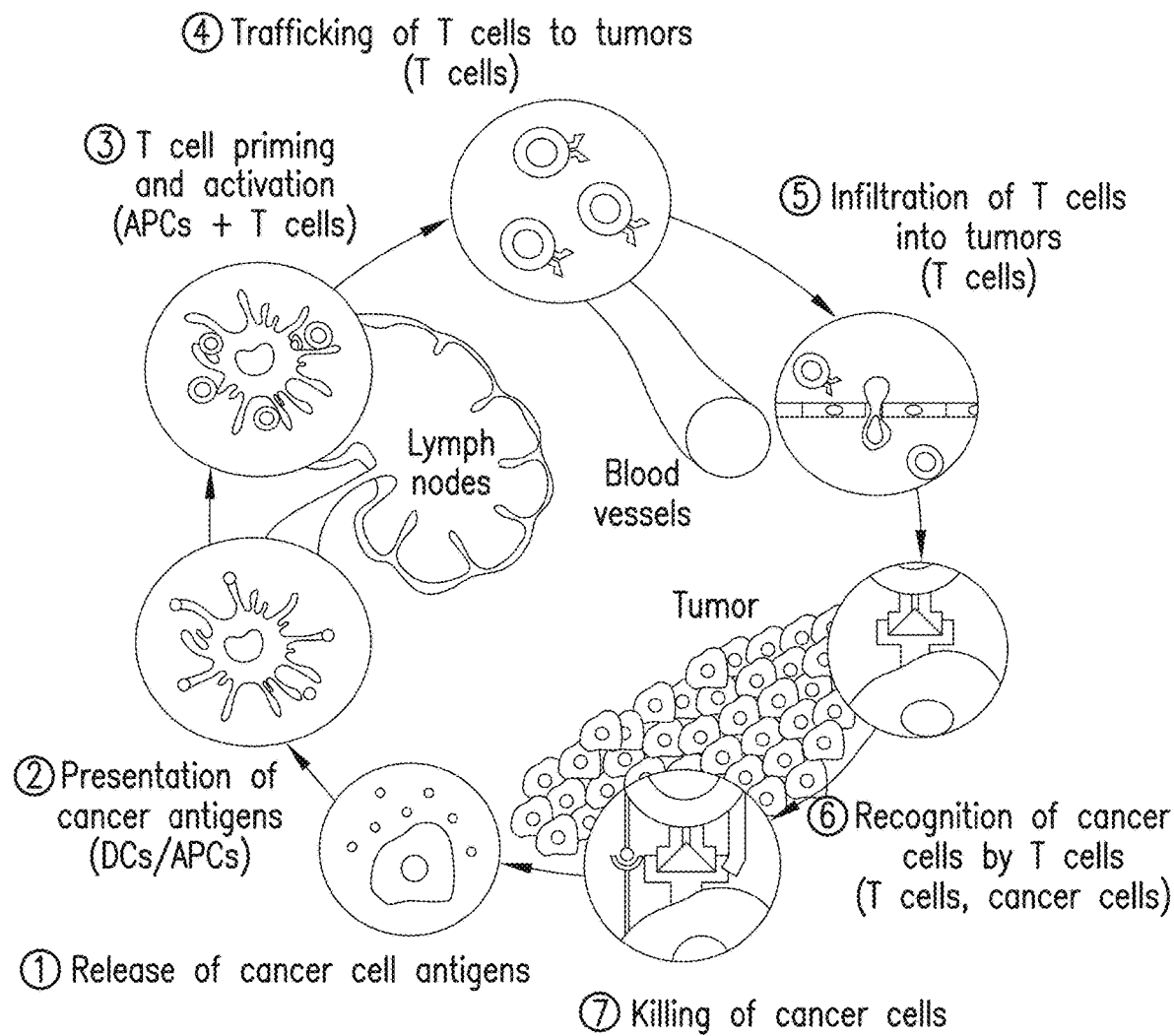
Figure 1D:
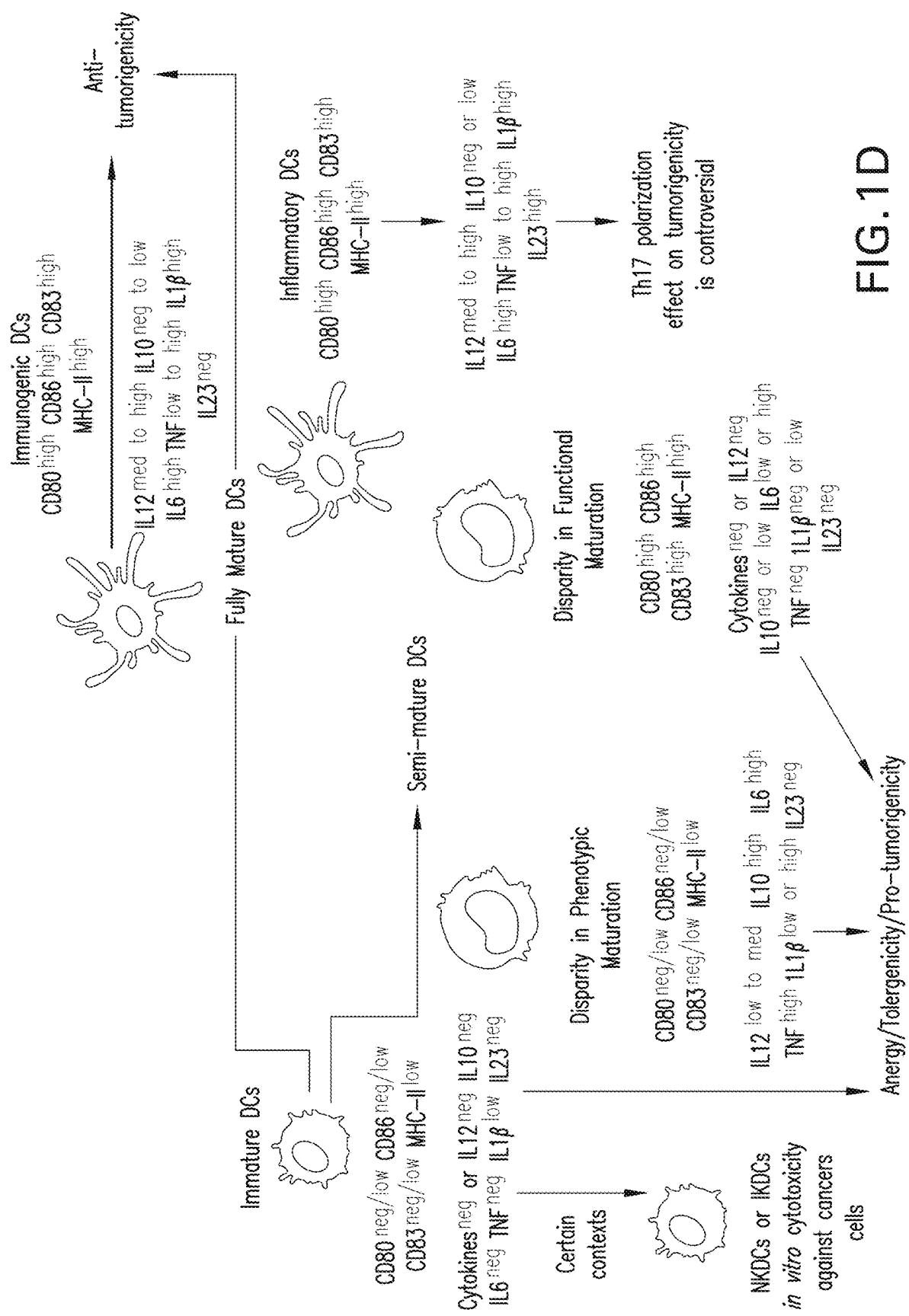
Figure 2A:
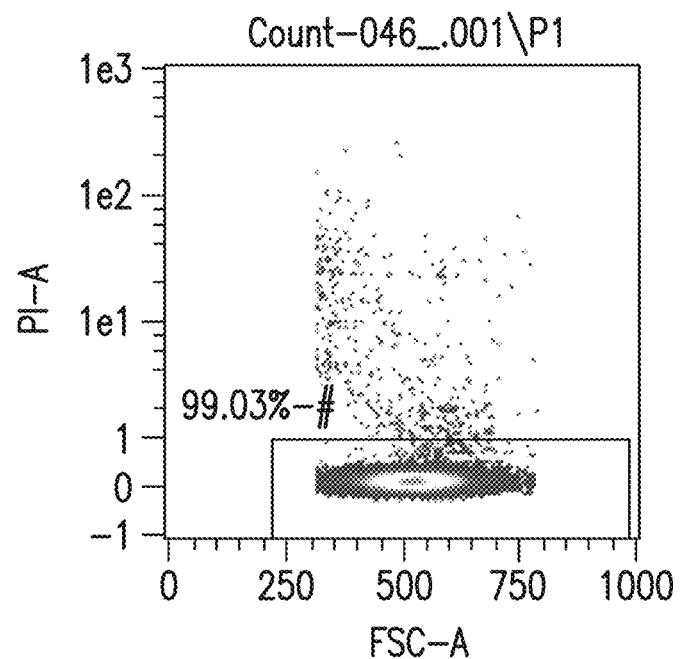
FIGS. 2A-F are flow cytometric images of CliniMACS isolated CD14+ monocytes for phenotyping and purity evaluation.
Figure 2B:
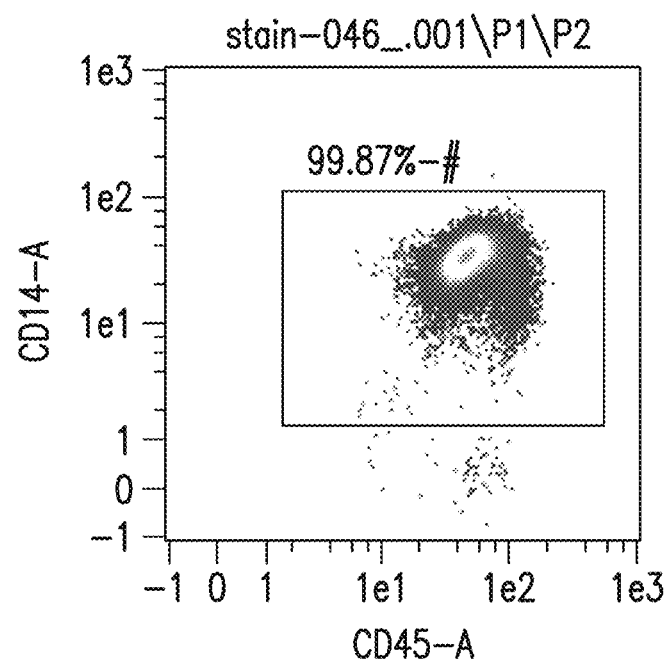
Figure 2C:
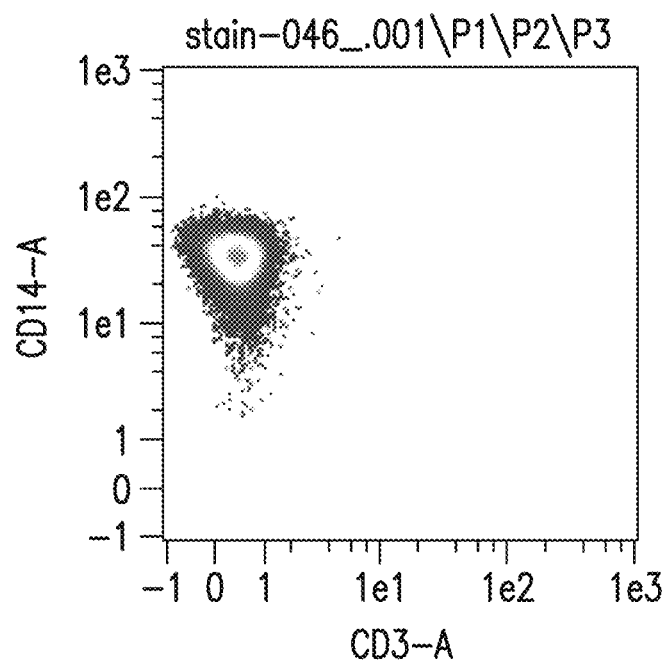
Figure 2D:
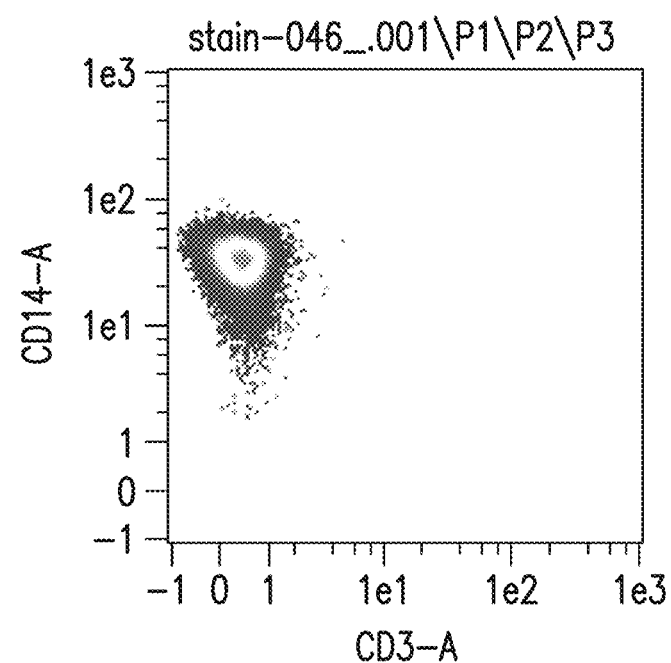
Figure 2E:
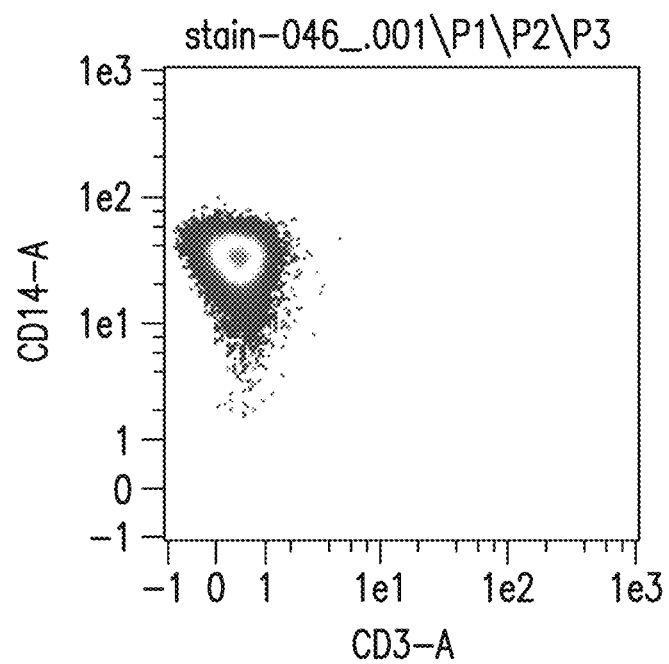
Figure 2F:
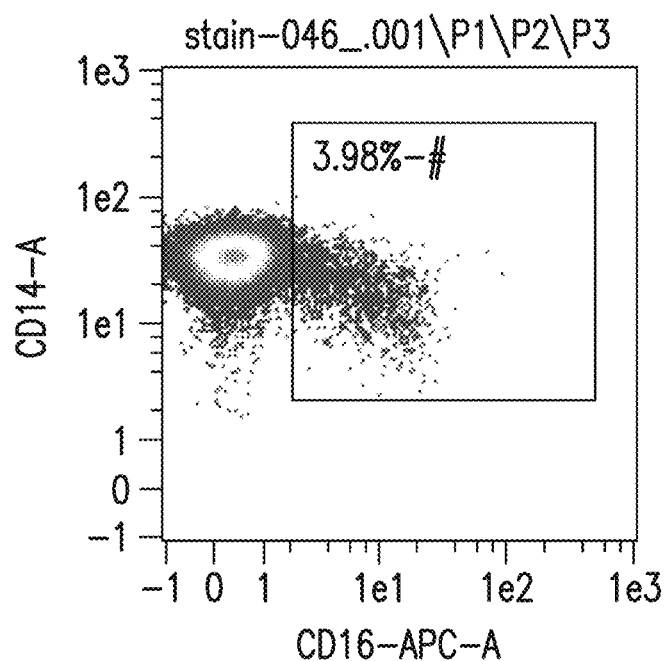
Figure 3A:
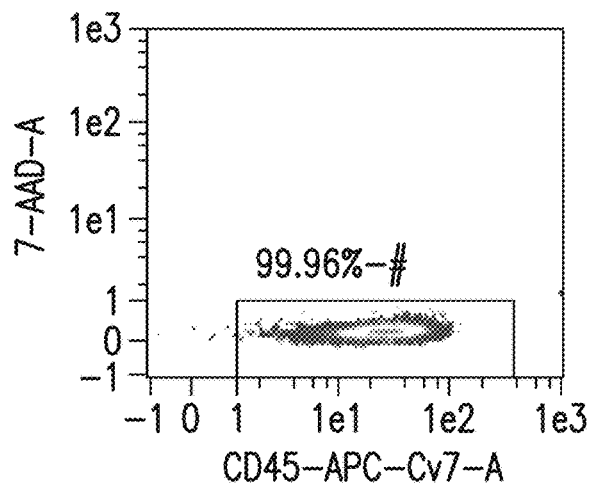
FIGS. 3A-P are flow cytometric images showing phenotyping of a sample of immature allo dendritic cells (alloDCs). Illustrating that the sample was analyzed for the following markers: Linage negative: (CD3−, CD56−, CD19−, CD66b−), CD45+, CD14−, CD40L+, CXL13+, CD1c+, CD11b+, CD11c+, HLA-DR+, CD86+, CD80low, CD83−, CD16Low, CD33+, CD163−, CD206+, CD209, CD40L.
Figure 3B:
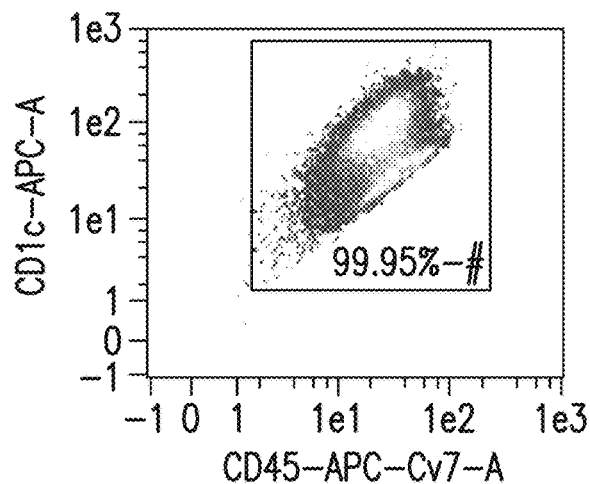
Figure 3C:
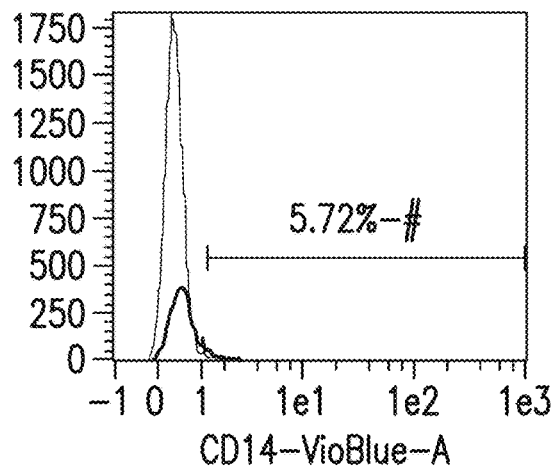
Figure 3D:
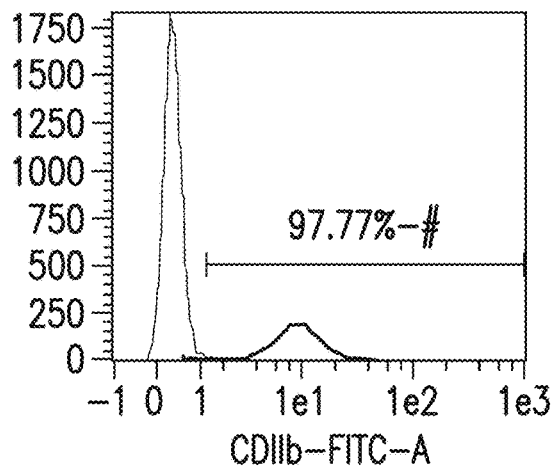
Figure 3E:
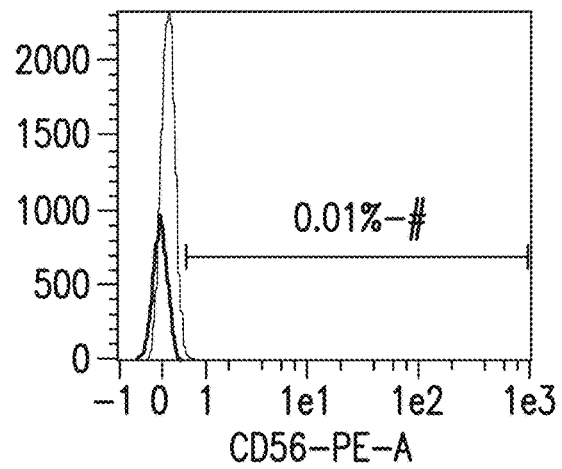
Figure 3F:
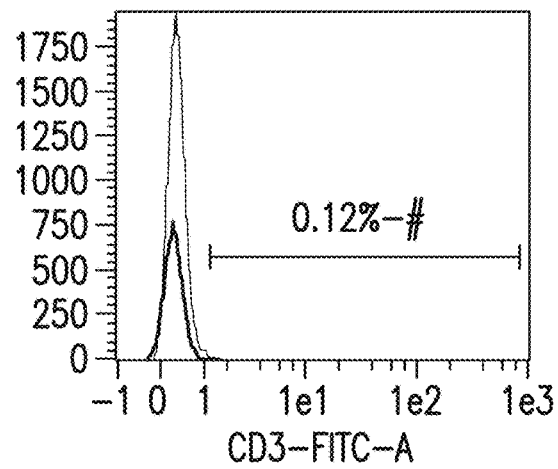
Figure 3G:
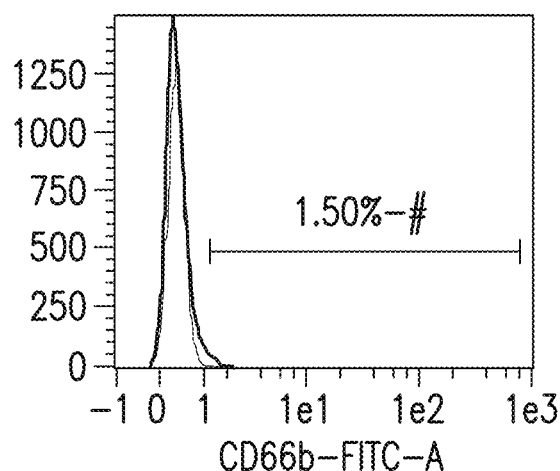
Figure 3H:
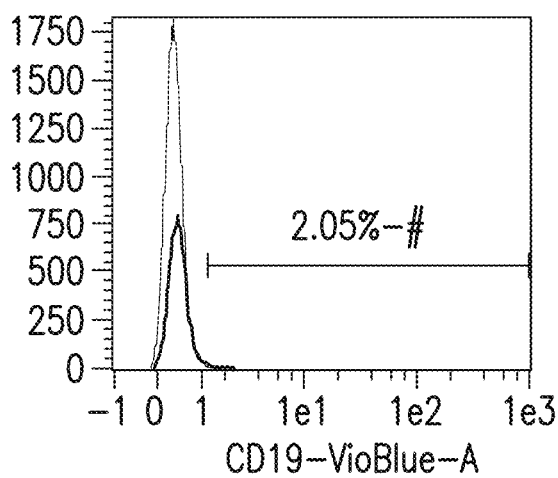
Figure 3I:
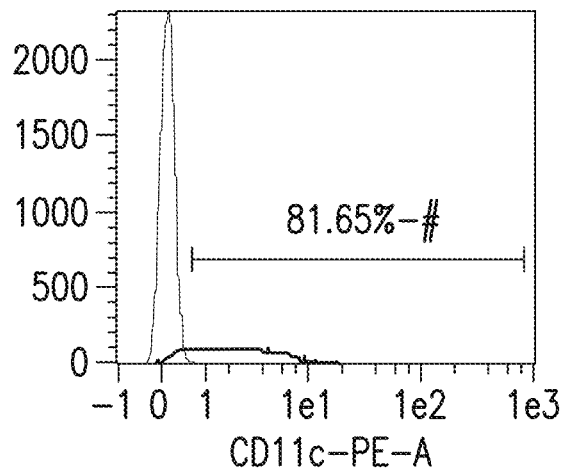
Figure 3J:
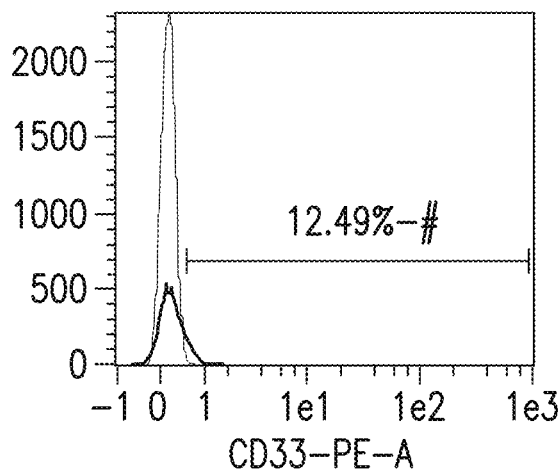
Figure 3K:
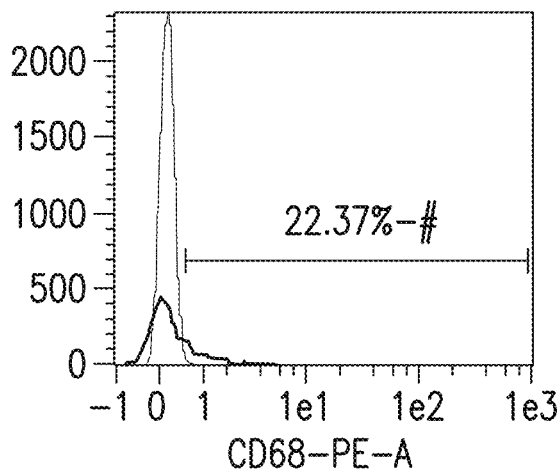
Figure 3L:
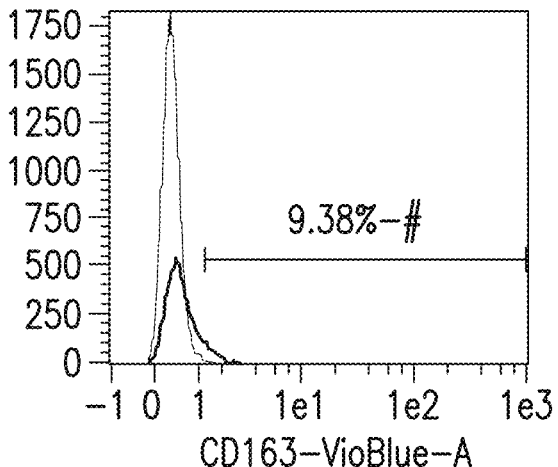
Figure 3M:
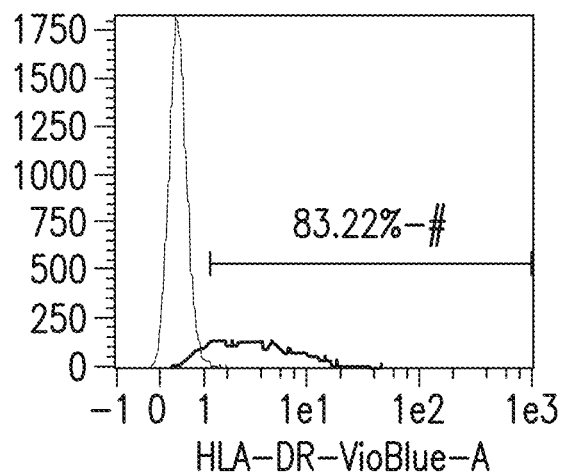
Figure 3N:
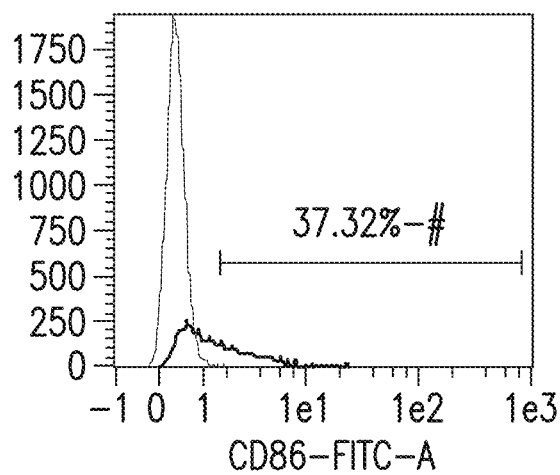
Figure 3O:
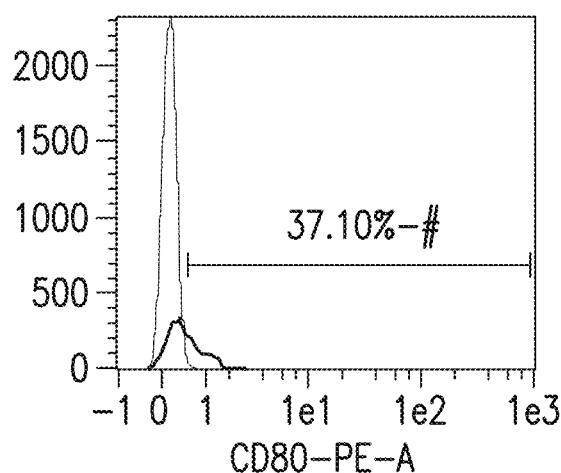
Figure 3P:
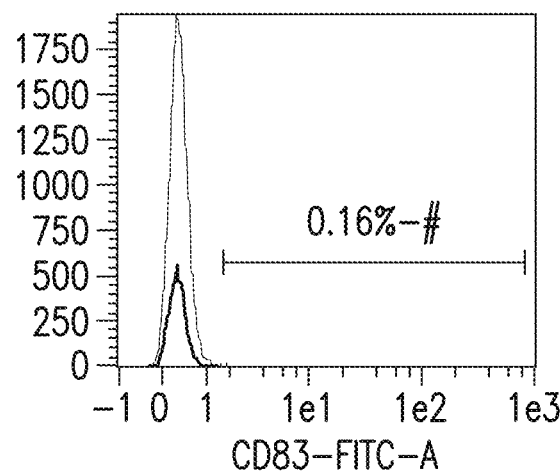

A description of the various stages of dendritic cells and maturation/activation factors is shown in FIG. 1D (See, Front Immunol. 2013; 4:438, which is hereby incorporated by reference in its entirety).

In some embodiments, the recombinant DCs are matured by the contacting the cells with maturation factors after loading with tumor cell lysate and/or antigen. Such maturation factors include at least: IL-1β, IL-6, TNF-α, and PGE2, or any combination thereof. In some embodiments, the recombinant DCs are matured by the contacting the cells with maturation factors prior to being contacted with tumor cell lysate and/or antigen. In some embodiments, the DCs are matured with the maturation factors and are not contacted with tumor cell lysate and/or antigen. In some embodiments, recombinant dendritic cells are cultured or incubated with a cytokine selected from the group consisting of IL-4, GM-CSF, IL-13, IFN-γ, Flt-31, SCF, and TNF-α.

Abbreviations

WBC: White Blood Cell
IPA: 70% Isopropyl Alcohol
QA: Quality Assurance
QC: Quality Control
Vol.: Volume
RT: Room Temperature
DC: Dendritic Cells
imDC: Immature Dendritic Cells
mDC: Mature Dendritic Cells
AlloDC: Allogeneic Dendritic Cells
MCV: MalCancerVac
GM-CSF: Granulocyte-Macrophage Colony-Stimulating Factor
IL-4: Interleukin 4
IL-1β: Interleukin 1β
IL-15: Interleukin 15
TNFα: Tumor Necrosis Factor α
pIC: Polyinosinic: Polycytidylic acid
IFN-α: Interferon α
IFN-γ: Interferon γ
CXCL13: C—X—C Motif Chemokine Ligand 13
CD40L: CD40 ligand
MAGE: melanoma-associated antigen
MOI: Multiplicity of Infection As used in this application and in the claims, the singular forms "a," "an," and "the" include the plural forms unless the context clearly dictates otherwise. Additionally, the term "includes" means "comprises."

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "about" when immediately preceding a numerical value means a range of plus or minus 10% of that value, e.g, "about 50" means 45 to 55, "about 25,000" means 22,500 to 27,500, etc, unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g, more than 49.5 to less than 52.5. Furthermore, the phrases "less than about" a value or "greater than about" a value should be understood in view of the definition of the term "about" provided herein. Additionally, if a range is written as "about X to Y" the "about" modifies both the X and the Y values unless context indicates otherwise.

The terms "administer," "administering" or "administration" as used herein refer to either directly administering a compound, cell, composition, or pharmaceutical composition, which can also referred to as an agent of interest. In some embodiments, the compositions have been sterilized or filtered to remove any viral or bacterial particles.

The terms "co-administration" or the like, are meant to encompass administration of the selected therapeutic agents to a single patient, and are intended to include treatment regimens in which the agents are administered by the same or different route of administration or at the same or different time.

A "therapeutically effective amount" of a composition is an amount sufficient to achieve the desired effect, i.e., to ameliorate, prevent or improve an unwanted condition, disease or symptom of a patient. The activity contemplated by the present methods may include both therapeutic and/or prophylactic treatment, as appropriate. The specific dose can be determined by the particular circumstances surrounding the case, including, for example, the therapeutic administered, the route of administration, and the condition being treated. The effective amount administered may be determined by a physician in the light of the relevant circumstances, including the condition to be treated, the choice of the therapeutic to be administered, and the chosen route of administration.

The term "inhibit" includes the administration of a therapeutic of embodiments herein to prevent the onset of the symptoms, alleviating the symptoms, or eliminating the disease, condition or disorder.

By "pharmaceutically acceptable", it is meant the carrier, diluent or excipient must be compatible with the other ingredients of the therapeutic and not deleterious to the recipient thereof.

The terms "treat," "treated," or "treating" as used herein refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. Beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

Disclosed herein are methods and compositions for treating cancer by eliciting an immune response by administering dendritic cells expressing heterologous proteins. In some embodiments, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments the dendritic cells will be allogeneic as to the subject they are administered to, and as such, are not restricted by HLA expression. The allogeneic nature of the cells as compared to the subject is an added advantage to mount an improved anti-tumor effect.

In some embodiments, the dendritic cells can be autologous to the subject that they are administered to.

Thus, while not wishing to be bound by theory, aspects of the present invention relates to providing dendritic cells expressing heterologous proteins (e.g. recombinant alloDCs) to a patient, to elicit an improved immune response to cancer (tumor) in the patient. The methods and compositions described herein have many advantages over previous compositions and methods, including the lack of co-culturing on feeder cells, as well as to minimize risks of contamination of the cellular composition due to the short in vitro culture/incubation time for recombinant alloDC and optionally loading with autologous or "off the shelf" antigens, and ease and speed of preparing and delivering the cellular composition to the patient, along with very minimal side effects from the cellular composition, which are typically only Grade 1 (or less side effects). These recombinant allo-DC cells and compositions provide the added benefit of eliciting both the cellular and humoral immune response in the patient. Furthermore, the host alloreactivity against the HLA-mismatched DCs will amplify the tumor-specific immune response. These methods also serve to provide a "vaccine effect" training the host, patient immune cells to similarly recognize and kill the cancer target, and boosting the host cellular and humoral responses. In some embodiments, the subject receiving the cells views the cells as foreign and will mount an immune response against the cells, which could be referred to as rejecting the cells. This "rejection" can amplify the tumor-specific immune response in the subject.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies may exist in a variety of forms including, for example, polyclonal antibodies, monoclonal antibodies, Fv, Fab and F(ab)2, as well as single chain antibodies and humanized antibodies.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term "antigen" as used herein is defined as a molecule that provokes an immune response. This immune response may involve either antibody production, or the activation of specific immunologically-competent cells, or both. The antigen can also be used in vitro to activate the DCs, which is comparable to an immune response. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the embodiments include, but are not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid. As described herein, the antigen can be a tumor cell lysate. Examples of tumor cell lysates include, but are not limited to, those described herein, lysates prepared from tumor biopsies or tumor resections. Methods of preparing lysates are known and any method can be used.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

Cancers that may be treated include tumors that are not vascularized, or not yet substantially vascularized, as well as vascularized tumors. Types of cancers to be treated with the recombinant dendritic cells described herein include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The term "anti-tumor effect" as used herein, refers to a biological effect that can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the recombinant cells and therapeutic compositions to prevent the occurrence of tumor in the first place.

As used herein, the term "autologous" is meant to refer to any material derived from the same individual to which it is later to be re-introduced into the individual.

"Allogeneic" refers to a sample (graft, cell, or population of cells) derived from a different animal of the same species to which the sample is later introduced. In some embodiments, the recombinant dendritic cells are completely HLA mismatched as compared to the subject receiving the recombinant dendritic cells, unlike the situations in renal and bone marrow transplantations where matching HLA-A, —B, and -DR are beneficial for graft survival. In the present methods for treating cancer and/or increasing and/or improving the immune response, the recombinant dendritic cells expressing CD40L, CXCL13, and optionally CD93 can attract T cells and, for example, generate humoral immune responses, which serve to target the cancer cells and bind to them, and kill them, releasing tumor cell antigens. This cycle repeats itself with the allogeneic recombinant dendritic cells, until they are killed by the host cell immune responses. This can happen, for example, within about 4 to about 7 days (and possibly during an extended range of about 4 to about 15 days). Thus, there is reduced or no risk for GVHD (Graft Versus Host Disease) with such a short life-span for the allogeneic recombinant DCs. However, in the process of recognizing and killing tumor cells and releasing antigens for that span of about 4 to about 7 days, the allogeneic cells can, in some embodiments, serve to vaccinate the host dendritic cells and other immune cells to recognize and kill the tumor cells. See additionally, review article *Cancer Sci.* 2019 January; 110(1):16-22, which is hereby incorporated by reference in its entirety. The induction of anti-tumor immunity is a cyclic process that can be self-propagating. It can amplify and extend T cell responses against cancer cells. It also contains several inhibitory factors itself to halt the cycle when the target cells (cancer cells) are eradicated. The cycle can be divided into 7 steps, as shown in FIG. 1C, starting with the release of cancer antigens from the cancer cells and ending with the killing of cancer cells. APC, antigen-presenting cell; DC, dendritic cell.

A "disease" is a state of health of a subject wherein the subject cannot maintain homeostasis, and wherein if the disease is not ameliorated then the animal's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. As used herein, a vector that encodes a protein of interest refers to a vector containing a nucleotide sequence that encodes for that protein or proteins.

As used herein, the term "exogenous" refers to any material introduced from or produced outside an organism, cell, tissue or system. A protein that is referred to as a heterologous protein is expressed by exogenous material (vectors, nucleotide sequences, and the like) that has been introduced into the organism, cell, tissue or system. For the avoidance of doubt, a heterologous protein, a heterologous vector, or heterologous nucleotide molecule is not the same as that may present in the native, unmodified genome of the organism, cell, tissue or system. A heterologous protein, vector, or nucleotide sequence that may have the same or similar to a sequence already present in the organism, cell, tissue, or system, is expressed from a location or sequence that is other than the native sequence found in the genome of that organism, cell, tissue, or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" or "Homology" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. An "isolated" biological component (such as a nucleic acid, protein or cell) has been substantially separated or purified away from other biological components (such as cell debris, other proteins, nucleic acids or cell types). Biological components that have been "isolated" include those components purified by standard purification methods.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Chemotherapy includes treatment with a chemical agent (such as a cytotoxic agent) with therapeutic utility for treating diseases characterized by abnormal cell growth, such as tumors, neoplasms, cancer and psoriasis. Examples of chemotherapies include, but are not limited to those described herein.

As used herein, recombinant generally refers to the following: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

As used herein, the following abbreviations for the commonly occurring nucleic acid bases are used. "A" refers to adenosine, "C" refers to cytosine, "G" refers to guanosine, "T" refers to thymidine, and "U" refers to uridine.

The term "leukocytes" or "white blood cell" as used herein refers to any immune cell, including monocytes, neutrophils, eosinophils, basophils, and lymphocytes. The term "lymphocytes" as used herein refer to cells commonly found in lymph, and include natural killer cells (NK cells), T-cells, and B-cells. It will be appreciated by one of skill in the art that the above listed immune cell types can be divided into further subsets.

The term "tumor infiltrating leukocytes" as used herein refers to leukocytes that are present in a solid tumor.

The term "blood sample" as used herein refers to any sample prepared from blood, such as plasma, blood cells isolated from blood, and so forth.

The term "purified sample" as used herein refers to any sample in which one or more cell subsets are enriched. A sample may be purified by the removal or isolation of cells based on characteristics such as size, protein expression, and so forth.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compositions, and additional pharmaceutical agents.

In general, the nature of a suitable carrier or vehicle for delivery will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, compositions, whether they be solutions, suspensions or other like form, may include one or more of the following: DMSO, sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

As used herein, immunodeficient means lacking in at least one essential function of the immune system. As used herein, an "immunodeficient" subject (such as a human) is one lacking specific components of the immune system or lacking function of specific components of the immune system (such as, for example, B cells, T cells, NK cells or macrophages). In some cases, an immunodeficient subject comprises one or more genetic alterations that prevent or inhibit the development of functional immune cells (such as B cells, T cells or NK cells). In some examples, the genetic alteration is in IL17 or IL17 receptor.

As used herein, immunosuppressed refers to a reduced activity or function of the immune system. A subject can be immunosuppressed, for example, due to treatment with an immunosuppressant compound or as a result of a disease or disorder (for example, immunosuppression that results from HIV infection or due to a genetic defect). In some cases, immunosuppression occurs as the result of a genetic mutation that prevents or inhibits the development of functional immune cells, such as T cells.

Examples of types of cancer and proliferative disorders that can be treated with an effective amount of recombinant dendritic cellular compositions and related methods described herein include, but are not limited to, fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilm's tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. The treatment and/or prevention of cancer includes, but is not limited to, alleviating one or more symptoms associated with cancer, the inhibition or reduction of the progression of cancer, the promotion of the regression of cancer, and/or the promotion of the immune response.

In certain other embodiments, a "therapeutically effective amount" is the amount of the recombinant dendritic cellular composition that results in a reduction of the tumor, growth or spread of cancer by at least 2.5%, at least 5%, at least 10%, at least 15%, at least 25%, at least 35%, at least 45%, at least 50%, at least 75%, at least 85%, by at least 90%, at least 95%, or at least 99% in a patient or an animal administered a composition or cells described herein relative to the tumor growth or spread of cancer in a patient (or an animal) or a group of patients (or animals) not administered a composition or cells of the invention.

In some embodiments, the recombinant dendritic cellular compositions can be administered simultaneously with anti-microbial, anti-viral and other therapeutic agents. Alternatively, recombinant dendritic cellular compositions can be administered at selected times in advance of times when anti-microbial, anti-viral and other therapeutic agents are administered.

Combinations with Antibodies

In some embodiments, the recombinant dendritic cellular compositions can be administered simultaneously with antibodies specific for a selected cancer type. Alternatively, recombinant dendritic cellular compositions can be administered at selected times in advance of times when antibodies specific for a selected cancer type are administered. Antibodies specific for a selected cancer type include any antibody approved for treatment of cancer. Examples include trastuzumab (Herceptin) for breast cancer, rituximab (Rituxan) for lymphoma, and cetuximab (Erbitux) for head and neck squamous cell carcinoma.

Additional examples of such antibody agents include inhibitors of PD-1 or PD-L1 (B7-H1), such as anti-PD-1 antibodies, including nivolumab (Nivolumab from Bristol-Myers Squibb) and pembrolizumab/lambrolizumab, also known as MK-3475 (Keytruda from Merck), pidilizumab (Curetech), AMP-224 (Amplimmune), and anti-PD-L1 antibodies, including MPDL3280A (Roche), MDX-1105 (Bristol Myer Squibb), MEDI-4736 (AstraZeneca) and MSB-0010718 C (Merck). Other checkpoint inhibitors include antagonists of CTLA-4, such as anti-CTLA-4 antibodies. An exemplary anti-CTLA4 antibody is Yervoy™ (ipilimumab) marketed by Bristol-Myers Squibb. Other exemplary CTLA-4 antibodies include tremelimumab (Pfizer), Ticilimumab (AstraZeneca) and AMGP-224 (Glaxo Smith Kline). Combinations with any two of these antibodies may also be indicated in certain instances.

In some embodiments, dendritic cells are isolated from various sources, including peripheral blood mononuclear cells.

"Peripheral blood mononuclear cells," "PBMCs" or "mononuclear cells" refer to mononuclear cells separated from peripheral blood typically used for anti-cancer immunotherapy. The peripheral blood mononuclear cells can be obtained from human blood collected using known methods such as the Ficoll-Hypaque density gradient method.

According to one exemplary embodiment, "peripheral blood mononuclear cells" may be obtained from any suitable person. The source of the donor cells, including sources such as peripheral blood mononuclear cells, as used herein, can in some embodiments, be allogeneic to the recipient patient for isolation of the dendritic cells for use in the cancer treatment and immune stimulating methods described herein. Thus, In some embodiments, the donor inhibitory ligand mismatches with the patient (e.g. host) HLA.

In alternative embodiments, the source of the donor cells, including sources such as peripheral blood mononuclear cells, as used herein are autologous to the recipient patient for isolation of the dendritic cells for use in the cancer treatment and immune stimulating methods described herein.

Cell Sources

PBMCs can be isolated by Ficoll-Hypaque density gradient centrifugation of samples obtained from discarded, de-identified leukocyte reduction filters (American Red Cross), or blood donations from healthy volunteers with informed consent. Descriptions of cell populations, sources and methods for selecting or enriching for desired cell types can be found, for example in: U.S. Pat. No. 9,347,044. Populations of cells for use in the methods described herein for treating mammals must be species matched, such as human cells. The cells may be obtained from an animal, e.g., a human patient. If the cells are obtained from an animal, they may have been established in culture first, e.g., by transformation; or more preferably, they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these. In an illustrative embodiment, a cell population is subjected to negative selection for depletion of non-T cells and/or particular T cell subsets. Negative selection can be performed on the basis of cell surface expression of a variety of molecules, including B cell markers such as CD19, and CD20; monocyte marker CD14; the NK cell marker CD56. Alternately, a cell population may be subjected to negative selection for depletion of non-CD34.sup.+ hematopoietic cells and/or particular hematopoietic cell subsets. Negative selection can be performed on the basis of cell surface expression of a variety of molecules, such as a cocktail of antibodies (e.g., CD2, CD3, CD11b, CD14, CD15, CD16, CD19, CD56, CD123, and CD235a) which may be used for separation of other cell types, e.g., via MACS or column separation.

Populations of cells include peripheral blood mononuclear cells, whole blood or fractions thereof containing mixed populations, spleen cells, bone marrow cells, tumor infiltrating lymphocytes, cells obtained by leukapheresis, biopsy tissue, lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

Methods of obtaining populations of cells comprising a monocytes (to be matured into DCs) or dendritic cells are well known in the art. For example, peripheral blood mononuclear cells (PBMC) can be obtained as described according to methods known in the art. Examples of such methods are described for example in: Nair, Smita et al. *Current protocols in immunology* vol. Chapter 7 (2012): Unit 7.32. doi:10.1002/0471142735.im0732s99.

It is also possible to obtain a cell sample from a subject, and then to enrich it for a desired cell type. For example, PBMCs can be isolated from blood as described herein. Counter-flow centrifugation (elutriation) can be used to enrich for monocytes or dendritic cells from PBMCs. Cells can also be isolated from other cells using a variety of techniques, such as isolation and/or activation with an antibody binding to an epitope on the cell surface of the desired cell type, for example, some T-cell isolation kits use antibody conjugated beads to both activate the cells and then allow column separation with the same beads. Another method that can be used includes negative selection using antibodies to cell surface markers to selectively enrich for a specific cell type without activating the cell by receptor engagement.

Bone marrow cells (BM cells) may be obtained from iliac crest, femora, tibiae, spine, rib or other medullary spaces. Bone marrow may be taken out of the patient and isolated through various separations and washing procedures. A known procedure for isolation of bone marrow cells comprises the following steps: a) centrifugal separation of bone marrow suspension in three fractions and collecting the intermediate fraction, or buffycoat; b) the buffycoat fraction from step (a) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells. Additionally, BM cells can be collected by mobilization followed by leukapheresis.

Dendritic cells (DCs) are the sentinel antigen presenting cells of the immune system. These cells have the capacity to acquire antigenic material from their environment and to subsequently initiate vigorous immune responses, and are ideal candidates to deliver vaccines for cancer immunotherapy. Dendritic cells comprise a heterogeneous cell population with distinctive morphology and a widespread tissue distribution. DCs exhibit cell surface markers, such as $CD1c^+$, $CD14^+$, $CD141^+$, $CD16^+$, or $HLA-DR^+$.

In particular, dendritic cells act as an antigen-presenting cell by endocytosis of exogeneous proteins which are then processed and presented as epitopes on their surface in conjunction with MHC class I and II antigens. The antigen presenting dendritic cells can be recognized by cytotoxic T cells and T-helper cells. The maturation state of the dendritic cells is important for their phagocytic/endocytic activity. Immature dendritic cells are typically the most efficient cells for loading antigens.

Immature dendritic cells refer to dendritic cells in which the expression of certain cell markers CD1a, CD14 and CD83 is characterized by a high expression of CD1a (more than 50% of DC's in the population are positive for CD1a), no expression or low expression of CD14 (less than 15% of DC's in the population are positive for CD14) and low expression of CD83 (less than 25% of DC's in the population are positive for CD83).

In some embodiments, DCs are obtained from any tissue where they reside, including non-lymphoid tissues such as the epidermis of the skin (Langerhans cells) and lymphoid tissues such as the spleen, bone marrow, lymph nodes and thymus as well as the circulatory system including blood and peripheral blood. Because DCs occur in low numbers in any tissues in which they reside, DCs may be enriched or isolated for use. Any of a number of procedures entailing repetitive density gradient separation, positive selection, negative selection or a combination thereof may be used to obtain enriched populations of DCs. Once the DCs are obtained, they may be cultured in appropriate culture medium to expand the cell population and/or maintain the DCs in a state for optimal antigen uptake, processing and presentation.

In some embodiments, the DCs may be autologous to a subject suffering from cancer, that is, the DCs that are administered to the subject may be isolated from the same subject. In other embodiments, the DCs may be allogeneic to the subject suffering from cancer. In some embodiments, the DCs disclosed herein may be any sub-type, such as myeloid DCs, plasmacytoid DCs, interstitial DCs, lymphoid tissue resident DCs, follicular DCs, $CD14^+$ DCs, and the like.

In some embodiments, methods of developing genetically engineered/recombinant dendritic cells expressing CD40L, CXCL13, and optionally CD93, that may be used for cancer therapy are provided.

CD40L is a type II membrane protein of 35 kDa and a member of the tumor necrosis factor (TNF) gene family, is expressed on the surface of T cells upon antigen recognition. CD40L is critically involved in the activation of T cells necessary to induce an effective protective immunity against tumor self-antigens. (See, Front Immunol. 2011; 2:31, which is hereby incorporated by reference in its entirety). The full sequence information for human CD40L can be found at NCBI, Gene ID:959.

CXCL13 is a chemokine expressed in follicular stromal cells of lymphoid organs, macrophages in the peritoneal and pleural cavities and in myeloid dendritic cells. It has been shown to bind primarily to the G-protein coupled receptor CXCR5. CXCR5 is expressed on B cells and certain subsets of T cells (including follicular helper T cells, a subset of circulating memory CD4 T cells, and other populations of T cells not fully differentiated as T-helper 1 (Th1) or T-helper 2 (Th2). CXCL13 has demonstrated physiologic roles in co-localization of B and T cells by influencing homing of auto-reactive B1 cells to Peyer's patches and other sites of inflammation, and by playing a role in recruitment of Th cells to secondary lymphoid organs for T dependent antibody production. (See, Front Immunol. 2016; 7:225, which is hereby incorporated by reference in its entirety). The full sequence information for human CXCL13 can be found at NCBI, Gene ID:10563.

Human CD93 (hCD93) is type 1 transmembrane glycoprotein located on chromosome 20, p11.21. This protein is involved in cell-cell interaction during B cell development and phagocytosis. CD93 is expressed in myeloid lineages, hematopoietic stem cells, NK cells, platelets, microglia, and endothelial cells. The full sequence information for human CD93 can be found at NCBI, Gene ID:22918.

In some embodiments, a dendritic cell comprises one or more heterologous nucleic acid molecules encoding for CD40L and/or CXCL13. The heterologous nucleic acid molecule encoding CD40L may be from any source, such as human, mouse, rat, or pig, or any other mammal. Human CD40L nucleic acid sequence is disclosed as SEQ ID NO: 1. Similarly, the heterologous nucleic acid molecule encoding CXCL13 may be from any source, such as human, mouse, rat, or pig, or any other mammal. Human CXCL13 nucleic acid sequence is disclosed as SEQ ID NO: 2.

In some embodiments, the dendritic cells may further comprise heterologous nucleic acid molecule encoding CD93. The heterologous nucleic acid molecule encoding CD93 may be from any source, such as human, mouse, rat, or pig, or any other mammal. Human CD93 nucleic acid sequence is disclosed as SEQ ID NO: 3.

The nucleic acid sequences encoding the proteins, however, can be other sequences due to the degenerate nature of the genetic code. These nucleic acid sequences are non-limiting examples and other can be used.

The corresponding human amino acid sequences are as follows: human CD40L: SEQ ID NO:4; human CXCL13: SEQ ID NO:5; and human CD93:SEQ ID NO: 6. In some embodiments, the protein comprises a conservative substitution.

The following sequences can be used as reference throughout the present application as appropriate:

In some embodiments, human CD40L is encoded by:

(SEQ ID NO: 1)
ATGATCGAAACATACAACCAAACTTCTCCCCGATCTGCGGCCACTGGACT
GCCCATCAGCATGAAAATTTTTATGTATTTACTTACTGTTTTTCTTATCA
CCCAGATGATTGGGTCAGCACTTTTTGCTGTGTATCTTCATAGAAGGTTG
GACAAGATAGAAGATGAAAGGAATCTTCATGAAGATTTTGTATTCATGAA
AACGATACAGAGATGCAACACAGGAGAAAGATCCTTATCCTTACTGAACT
GTGAGGAGATTAAAAGCCAGTTTGAAGGCTTTGTGAAGGATATAATGTTA
AACAAAGAGGAGACGAAGAAAGAAAACAGCTTTGAAATGCAAAAGGTGA
TCAGAATCCTCAAATTGCGGCACATGTCATAAGTGAGGCCAGCAGTAAAA
CAACATCTGTGTTACAGTGGGCTGAAAAAGGATACTACACCATGAGCAAC
AACTTGGTAACCCTGGAAAATGGGAAACAGCTGACCGTTAAAAGACAAGG
ACTCTATTATATCTATGCCCAAGTCACCTTCTGTTCCAATCGGGAAGCTT
CGAGTCAAGCTCCATTTATAGCCAGCCTCTGCCTAAAGTCCCCCGGTAGA
TTCGAGAGAATCTTACTCAGAGCTGCAAATACCCACAGTTCCGCCAAACC
TTGCGGGCAACAATCCATTCACTTGGGAGGAGTATTTGAATTGCAACCAG
GTGCTTCGGTGTTTGTCAATGTGACTGATCCAAGCCAAGTGAGCCATGGC
ACTGGCTTCACGTCCTTTGGCTTACTCAAACTC

In some embodiments, human CXCL13 is encoded by:

(SEQ ID NO: 2)
ATGAAGTTCATCTCGACATCTCTGCTTCTCATGCTGCTGGTCAGCAGCCT
CTCTCCAGTCCAAGGTGTTCTGGAGGTCTATTACACAAGCTTGAGGTGTA
GATGTGTCCAAGAGAGCTCAGTCTTTATCCCTAGACGCTTCATTGATCGA
ATTCAAATCTTGCCCCGTGGGAATGGTTGTCCAAGAAAAGAAATCATAGT
CTGGAAGAAGAACAAGTCAATTGTGTGTGGACCCTCAAGCTGAATGGA
TACAAAGAATGATGGAAGTATTGAGAAAAAGAAGTTCTTCAACTCTACCA
GTTCCAGTGTTTAAGAGAAAGATTCCC

In some embodiments, human CD93 is encoded by:

(SEQ ID NO: 3)
ATGGCCACCTCCATGGGCCTGCTGCTGCTGCTGCTGCTGCTCCTGACCCA
GCCCGGGGCGGGGACGGGAGCTGACACGGAGGCGGTGGTCTGCGTGGGA
CCGCCTGCTACACGGCCCACTCGGGCAAGCTGAGCGCTGCCGAGGCCCAG
AACCACTGCAACCAGAACGGGGGCAACCTGGCCACTGTGAAGAGCAAGGA
GGAGGCCCAGCACGTCCAGCGAGTACTGGCCCAGCTCCTGAGGCGGGAGG
CAGCCCTGACGGCGAGGATGAGCAAGTTCTGGATTGGGCTCCAGCGAGAG
AAGGGCAAGTGCCTGGACCCTAGTCTGCCGCTGAAGGGCTTCAGCTGGGT
GGGCGGGGGGAGGACACGCCTTACTCTAACTGGCACAAGGAGCTCCGGA
ACTCGTGCATCTCCAAGCGCTGTGTGTCTCTGCTGCTGGACCTGTCCCAG
CCGCTCCTTCCCAGCCGCCTCCCCAAGTGGTCTGAGGGCCCCTGTGGGAG
CCCAGGCTCCCCCGGAAGTAACATTGAGGGCTTCGTGTGCAAGTTCAGCT
TCAAAGGCATGTGCCGGCCTCTGGCCCTGGGGGGCCCAGGTCAGGTGACC
TACACCACCCCTTCCAGACCACCAGTTCCTCCTTGGAGGCTGTGCCCTT
TGCCTCTGCGGCCAATGTAGCCTGTGGGGAAGGTGACAAGGACGAGACTC
AGAGTCATTATTTCCTGTGCAAGGAGAAGGCCCCCGATGTGTTCGACTGG
GGCAGCTCGGGCCCCTCTGTGTCAGCCCCAAGTATGGCTGCAACTTCAA
CAATGGGGCTGCCACCAGGACTGCTTTGAAGGGGGGGATGGCTCCTTCC
TCTGCGGCTGCCGACCAGGATTCCGGCTGCTGGATGACCTGGTGACCTGT
GCCTCTCGAAACCCTTGCAGCTCCAGCCCATGTCGTGGGGGGCCACGTG
CGTCCTGGGACCCCATGGGAAAAACTACACGTGCCGCTGCCCCCAAGGGT
ACCAGCTGGACTCGAGTCAGCTGGACTGTGTGGACGTGGATGAATGCCAG
GACTCCCCCTGTGCCCAGGAGTGTGTCAACACCCCTGGGGGCTTCCGCTG
CGAATGCTGGGTTGGCTATGAGCCGGGCGGTCCTGGAGAGGGGGCCTGTC
AGGATGTGGATGAGTGTGCTCTGGGTCGCTCGCCTTGCGCCCAGGGCTGC
ACCAACACAGATGGCTCATTTCACTGCTCCTGTGAGGAGGGCTACGTCCT
GGCCGGGGAGGACGGGACTCAGTGCCAGGACGTGGATGAGTGTGTGGGCC
CGGGGGGCCCCCTCTGCGACAGCTTGTGCTTCAACACACAAGGGTCCTTC
CACTGTGGCTGCCTGCCAGGCTGGGTGCTGGCCCCAAATGGGGTCTCTTG
CACCATGGGGCCTGTGTCTCTGGGACCACCATCTGGGCCCCCCGATGAGG
AGGACAAAGGAGAGAAAGAAGGGAGCACCGTGCCCCGTGCTGCAACAGCC
AGTCCCACAAGGGGCCCCGAGGGCACCCCCAAGGCTACACCCACCACAAG
TAGACCTTCGCTGTCATCTGACGCCCCCATCACATCTGCCCCACTCAAGA
TGCTGGCCCCAGTGGGTCCCCAGGCGTCTGGAGGGAGCCCAGCATCCAT
CACGCCACAGCTGCCTCTGGCCCCCAGGAGCCTGCAGGTGGGACTCCTC
CGTGGCCACACAAAACAACGATGGCACTGACGGGCAAAAGCTGCTTTTAT
TCTACATCCTAGGCACCGTGGTGGCCATCCTACTCCTGCTGGCCCTGGCT
CTGGGGCTACTGGTCTATCGCAAGCGGAGAGCGAAGAGGGAGGAGAAGAA
GGAGAAGAAGCCCCAGAATGCGGCAGACAGTTACTCCTGGGTTCCAGAGC
GAGCTGAGAGCAGGGCCATGGAGAACCAGTACAGTCCGACACCTGGGACA
GACTGC

In some embodiments, human CD40L comprises an amino acid sequence of:

(SEQ ID NO: 4)
MIETYNQTSPRSAATGLPISMKIFMYLLTVFLITQMIGSALFAVYLHRRL
DKIEDERNLHEDFVFMKTIQRCNTGERSLSLLNCEEIKSQFEGFVKDIML
NKEETKKENSFEMQKGDQNPQIAAHVISEASSKTTSVLQWAEKGYYTMSN
NLVTLENGKQLTVKRQGLYYIYAQVTFCSNREASSQAPFIASLCLKSPGR
FERILLRAANTHSSAKPCGQQSIHLGGVFELQPGASVFVNVTDPSQVSHG
TGFTSFGLLKL

In some embodiments, human CXCL13 comprises an amino acid sequence of:

(SEQ ID NO: 5)
MKFISTSLLLMLLVSSLSPVQGVLEVYYTSLRCRCVQESSVFIPRRFIDR

IQILPRGNGCPRKEIIVWKKNKSIVCVDPQAEWIQRMMEVLRKRSSSTLP

VPVFKRKIP

In some embodiments, human CD93 comprises an amino acid sequence of:

(SEQ ID NO: 6)
MATSMGLLLLLLLLLTQPGAGTGADTEAVVCVGTACYTAHSGKLSAAEAQ

NHCNQNGGNLATVKSKEEAQHVQRVLAQLLRREAALTARMSKFWIGLQRE

KGKCLDPSLPLKGFSWVGGGEDTPYSNWHKELRNSCISKRCVSLLLDLSQ

PLLPSRLPKWSEGPCGSPGSPGSNIEGFVCKFSFKGMCRPLALGGPGQVT

YTTPFQTTSSSLEAVPFASAANVACGEGDKDETQSHYFLCKEKAPDVFDW

GSSGPLCVSPKYGCNFNNGGCHQDCFEGGDGSFLCGCRPGFRLLDDLVTC

ASRNPCSSSPCRGGATCVLGPHGKNYTCRCPQGYQLDSSQLDCVDVDECQ

DSPCAQECVNTPGGFRCECWVGYEPGGPGEGACQDVDECALGRSPCAQGC

TNTDGSFHCSCEEGYVLAGEDGTQCQDVDECVGPGGPLCDSLCFNTQGSF

HCGCLPGWVLAPNGVSCTMGPVSLGPPSGPPDEEDKGEKEGSTVPRAATA

SPTRGPEGTPKATPTTSRPSLSSDAPITSAPLKMLAPSGSPGVWREPSIH

HATAASGPQEPAGGDSSVATQNNDGTDGQKLLLFYILGTVVAILLLLALA

LGLLVYRKRRAKREEKKEKKPQNAADSYSWVPERAESRAMENQYSPTPGT

DC.

In some embodiments, protein is at least, or about, 90, 91, 92, 93, 94, 95, 96, 97, 98, 99% homologous to the sequences provided herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The heterologous nucleic acid molecules can be introduced into dendritic cells by any known recombinant techniques known in the art, such as liposomal transfection, chemical transfection, transgenic DNA recombination, viral infection, transposon insertion, jumping gene insertion, micro-injection, electroporation, gene-gun penetration, and a combination thereof. In some embodiments, a recombinant adenoviral vector, a recombinant adeno-associated vector, a recombinant retroviral vector, a recombinant lentiviral vector, or a combination thereof, may be used to introduce the heterologous nucleic acid molecules.

In some embodiments, methods to express desired genes—CD40L, CXCL13, and CD93 may be used. Such methods include delivering CRISPR/Cas system, TALENs, and zinc-finger nucleases. For example, TALENs and CRISPR/Cas systems may be used to insert specific transcriptional regulatory elements upstream and downstream of a native gene. TALENs and CRISPR/Cas9 are capable of generating single or double stranded DNA breaks at specific loci. This stimulates homology directed repair (HDR) from an exogenous template allowing for precise insertion of transcriptional regulatory elements to activate the native genes. CRISPR/Cas nucleases may be delivered by using any gene delivery vectors, such as adenoviral vector, adeno-associated vector, retroviral vector, lentiviral vector, or a combination thereof.

In some embodiments, the genetically engineered DCs disclosed herein may be cultured in conventional nutrient media under ambient conditions, such as temperature, pH, and the like, and are apparent to those skilled in the art.

In some embodiments, the DCs overexpressing CD40L, CXCL13, and CD93 may be activated or pulsed by an antigen. In some embodiments, the antigen may be a tumor antigen or a viral antigen. Non-limiting examples of tumor antigen include antigen expressed by a colorectal cancer cell, a breast cancer cell, an ovarian cancer cell, a pancreatic cancer cell, a head and neck cancer cell, a bladder cancer cell, a liver cancer cell, a renal cancer cell, a melanoma cell, a gastrointestinal cancer cell, a prostate cancer cell, a small cell lung cancer cell, non-small cell lung cancer cell, a sarcoma cell, a glioblastoma cell, T- and B-cell lymphoma cell, a endometrial cancer cell, or a cervical cancer cell.

In some embodiments, the antigen may be a cancer (tumor) cell lysate, and the cancer cell lysate may be allogeneic or autologous to the dendritic cell. In some embodiments, the cancer cell lysate may be a melanoma cancer cell lysate, such as DDM-1.7 cell lysate, a DDM-1.13 cell lysate, or a combination thereof.

Numerous methods of pulsing or activating dendritic cells with antigen are known in the art. In some embodiments, the antigen may be added to cultured dendritic cells under conditions promoting viability of the cells, and the cells are then allowed sufficient time to take up and process the antigen, and express antigen peptides on the cell surface in association with either Class I or Class II MHC, a period of about 24 hours (from about 18 to about 30 hours, preferably 24 hours). Dendritic cells may also be exposed to antigen by transfecting them with DNA encoding the antigen. The DNA is expressed, and the antigen is presumably processed via the cytosolic/Class I pathway.

In some embodiments, isolated peptides may be used to pulse or activate DCs. Peptide is pulsed by any of a variety of methods, including incubation of the peptide with the dendritic cell, incubation of a protein comprising the peptide with DC, transduction of DC (or the progenitor expanded monocyte population) with a gene encoding the peptide (or a protein comprising the peptide), or the like. Typical antigens for use as peptides are derived from those expressed in a target cell such as a transformed cell, a cancer cell, a bacterial cell, a parasitically infected cell or a virally infected cell, or the like. Examples include, but are not limited to, carbohydrates, such as mucin, tumor antigens, peptides derived from a protein selected from the group consisting of HIV Gag, HIV Env, HER-2, MART-1, gp-100, PSA, HBVc, HBVs, HPV E6, HPV E7, tyrosinase, MAGE-1, trp-1, mycobacterial antigens, and CEA, as well as many others. Tumor antigens suitable for presentation include, but are not limited to, c-erb-β-2/HER2/neu, PEM/MUC-1, Int-2, Hst, BRCA-1, BRCA-2, truncated EGFRvIII, CEA, p53, ras, RK, Myc, Myb, OB-1, OB-2, BCR/ABL, GIP, GSP, RET, ROS, FIS, SRC, TRC, WTI, DCC, NF1, FAP, MEN-1, ERB-B1, MAGE-antigens, and idiotypic immunoglobulins (e.g., from a B cell of a non-Hodgkin's lymphoma patient). The antigen presenting activity of dendritic cells may be enhanced by co-culture with certain cytokines, such as TNF-α or IL-1α or IL-1β.

The activated dendritic cells disclosed herein may be present in a composition comprising physiologically acceptable carriers, excipients, adjuvants, or diluents. Neutral buffered saline or saline mixed with serum albumin are exemplary appropriate diluents. Suitable carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In some embodiments, the composition may comprise a tumor antigen or a viral antigen. In some embodiments, the composition is free of any heterologous antigen. In some embodiments, the composition comprises a population of at least about $10^5$ dendritic cells/mL, at least about $10^6$ cells/mL, at least about $10^7$ cells/mL, or more.

In some embodiments, the activated DCs may be frozen (cryopreserved) before administration into a subject. In some embodiments, the activated DCs may be frozen by suspending the cells in media containing at least 30% human-derived serum and/or plasma, and lowering the temperature of the suspension to at least −80° C., thereby freezing the DCs. In some embodiments, the freezing media is approximately 30% human-derived serum and/or plasma and approximately 10% of an agent that prevents ice crystal formation during freezing, e.g., DMSO. In a further embodiment, the DC suspension is maintained at −80° C. for at least 24 hours and then transferred to liquid nitrogen for the duration of the storage. In a further embodiment, the DC suspension is thawed at a temperature in the range of 34° to 41° C.

Also disclosed herein are methods to develop immature DCs from monocytes, and activating the immature DCs with allogenic or autologous tumor cell lysates. In some embodiments, the method includes: (a) isolating monocytes from a subject; (b) overexpressing one or more genes selected from CD40L, CXCL13, and CD93 in the isolated monocytes; and (c) differentiating the monocytes expressing one or more genes selected from CD40L, CXCL13, and CD93 into immature the dendritic cells in vitro. In some embodiments, the monocytes are $CD14^+$ monocytes. In some embodiments, the method comprises: differentiating monocytes heterologously expressing CD40L, CXCL13, and/or CD93 into immature the dendritic cells in vitro. In some embodiments, the monocytes are $CD14^+$ monocytes. In some embodiments, the cell is a CD34+ cell that is transduced and differentiated or expanded into a monocyte and then matured as provided herein. The different combinations of the heterologously expressed proteins are also described herein.

In some embodiments, monocytes are obtained from a variety of sources, such as leukapheresis of peripheral blood mononuclear cells from a patient, followed by elutriation of the isolated peripheral blood to provide isolated monocytes. The isolated monocytes may be genetically manipulated to express any one or combination of the heterologous CD40L, CXCL13, and CD93 proteins by techniques disclosed herein, such as liposomal transfection, chemical transfection, transgenic DNA recombination, viral infection, transposon insertion, jumping gene insertion, micro-injection, electroporation, gene-gun penetration, and a combination thereof. In some embodiments, a recombinant adenoviral vector, a recombinant adeno-associated vector, a recombinant retroviral vector, a recombinant lentiviral vector, or a combination thereof, may be used. Methods such as delivering CRISPR/Cas system, TALENs, and zinc-finger nucleases may also be used to overexpress any one or combination of the heterologous proteins CD40L, CXCL13, and CD93.

In some embodiments, the recombinant monocytes expressing CD40L, CXCL13, and optionally CD93, are grown in the presence of IL-3, causing the monocytes to proliferate, yielding an expanded population of monocytes. The expanded population of monocytes is differentiated into immature dendritic cells, e.g., by culturing the expanded population of cells with GM-CSF and IL-4 (to produce baseline or Type I DCs) and, optionally, TNF-α, IL-1β, IL-6, IFN-α, IFN-γ, and $PGE_2$.

In some embodiments, the recombinant allogeneic immature dendritic cells may be activated or pulsed by an antigen. In some embodiments, the antigen may be a tumor antigen or a viral antigen. In some embodiments, the antigen may be a cancer cell lysate, and the cancer cell lysate may be allogenic or autologous to the immature dendritic cell. In some embodiments, the cancer cell lysate may be a melanoma cancer cell lysate, such as DDM-1.7 cell lysate, a DDM-1.13 cell lysate, or a combination thereof. In some embodiments, the cells are not activated or pulsed by an antigen.

In some embodiments, the activated immature DCs disclosed herein may be present in a composition comprising physiologically acceptable carriers, excipients, adjuvants, or diluents. Neutral buffered saline or saline mixed with serum albumin are exemplary appropriate diluents. In some embodiments, the activated immature DCs may be frozen before administration into a subject. The cells can be thawed prior to being administered to the subject.

Also disclosed herein are methods of treating cancer in a subject. In some embodiments, a method of treating cancer in a subject comprises administering to the subject a composition comprising a recombinant dendritic cell, wherein the dendritic cell heterologously expresses one or more proteins selected from CD40L, CXCL13, and optionally CD93. As described herein, the cells can be allogeneic to the subject. The cells, in some embodiments, can be autologous to the subject.

In some embodiments, a method of eliciting immune response in a subject suffering from cancer comprises administering to the subject a composition comprising a dendritic cell, wherein the dendritic cell heterologously expresses one or more proteins selected from CD40L, CXCL13, and optionally CD93. In some embodiments, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments, a method of providing cancer vaccine to a subject suffering from cancer comprises administering to the subject a composition comprising a dendritic cell, wherein the dendritic cell heterologously express one or more proteins selected from CD40L, CXCL13, and optionally CD93. In some embodiments, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments, the dendritic cells (heterologously expressing CD40L, CXCL13, and/or CD93) administered are allogeneic to the subject. In some embodiments, the dendritic cells (heterologously CD40L, CXCL13, and/or CD93) administered are autologous to the subject. In some embodiments, the dendritic cells administered are immature dendritic cells heterologously expressing CD40L, CXCL13, and/or CD93. In some embodiments, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments, the subject is suffering from a cancer selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma, acute lymphocytic leukemia, acute myelocytic leukemia, chronic leukemia, polycythemia vera, lymphoma, multiple myeloma, Waldenstrom's macroglobulinemia, heavy chain disease, and combinations thereof.

In additional embodiments, the cancer is a solid tumor selected from the group consisting of fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In additional embodiments, the method further comprises at a time-frame of from 4-14 days following administration of the recombinant dendritic cells, administering the patient an immune check-point inhibitor, including any one or combination of two check point inhibitors, including an inhibitor of PD-1 or PD-L1 (B7-H1), such as an anti-PD-1 antibody, including nivolumab (Nivolumab from Bristol-Myers Squibb), pembrolizumab/lambrolizumab, also known as MK-3475 (Keytruda from Merck), pidilizumab (Curetech), AMP-224 (Amplimmune), or an anti-PD-L1 antibody, including MPDL3280A (Roche), MDX-1105 (Bristol Myer Squibb), MEDI-4736 (AstraZeneca) and MSB-0010718 C (Merck), an antagonist of CTLA-4, such as an anti-CTLA-4 antibody including anti-CTLA4 antibody Yervoy™ (ipilimumab, Bristol-Myers Squibb), tremelimumab (Pfizer), Ticilimumab (AstraZeneca) or AMGP-224 (Glaxo Smith Kline), or a tumor specific antibody trastuzumab (Herceptin) for breast cancer, rituximab (Rituxan) for lymphoma, or cetuximab (Erbitux).

In additional embodiments, the treatment, administration, or increasing the immune response is repeated periodically for time frames, such as those in Examples 1-3, for as long as the patient exhibits improvement or stable/non-progressing disease.

In additional embodiments, the treatment, administration, or increasing the immune response is repeated periodically for time frames of from once every 5 days, once every week, once every 14 days, once every 21 days, to once a month, to once every two months, to once every 3 months, to once every 4 months, to once every 5 months, to once every 6 months, or once every 7 months, or once every 8 months, or once every 9 months, or once every 10 months, or once every 11 months, or once annually as a maintenance treatment, for as long as the patient exhibits improvement or stable/non-progressing disease.

In some embodiments, the recombinant dendritic cells (heterologously CD40L, CXCL13, and/or CD93) administered to the subject are not activated or pulsed with an antigen prior to administration. In some embodiments, the dendritic cells may be administered in a composition comprising adjuvants, cytokines, and interleukins that may help in eliciting immune response. In some embodiments, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments, the method further comprises: (a) obtaining a protein expression profile of a resected tumor or biopsy sample from the subject;
  (b) comparing the protein expression profile of the resected tumor or biopsy sample to the protein expression profile of a melanoma cell lysate; and
  (c) if at least three markers in the protein expression profile of the resected tumor or biopsy sample match with the protein expression profile of the melanoma cell lysate, then co-culturing the dendritic cell overexpressing CD40L, CXCL13, and optionally CD93 with the melanoma cell lysate to activate the dendritic cell, and administering to the subject a composition comprising the activated dendritic cell; and
  (d) if at least three markers in the protein expression profile of the resected tumor or biopsy sample do not match with the protein expression profile of the melanoma cell lysate, then co-culturing the dendritic cell overexpressing CD40L, CXCL13, and optionally CD93 with the tumor or biopsy sample to activate the dendritic cell, and administering to the subject a composition comprising the activated dendritic cell.

In some embodiments, the methods provided for herein further comprise, screening a protein expression profile of a resected tumor or biopsy sample from the subject to cross-match a protein expression profile of an allogeneic tumor lysate prior to administration; and administering an allogeneic tumor lysate activated dendritic cell or activated dendritic cell composition if at least three fragments of the protein expression profile of the resected tumor or biopsy sample cross-match the protein expression profile of the allogeneic tumor lysate. As used herein, the term "cross-match" refers to comparing the protein expression profile of one sample against another, such as the tumor lysate as compared to the biopsy or resected tumor sample. If a protein fragment is found in both the lysate and the sample it is said to match.

In some embodiments of the above-described method, the DCs heterologously express CD40L and CXCL13. In some embodiments, the DCs heterologously express CD40L, CXCL13, and CD93. In some embodiments, the DCs heterologously express CD40L and CD93. In some embodiments, the DCs heterologously express CXCL13 and CD93. In some embodiments, the DCs do not heterologously express CD93.

In some embodiments, the protein expression profile is measured or compared by well-known techniques in the art, such as protein arrays, proteomics, mass spectroscopy (MALDI-MS), and the like. In some embodiments, gene expression profile may be used in place of protein expression profile for comparison. Gene expression profile can be obtained using well-known techniques in the art, such as gene arrays, microarrays, RT-PCR, and the like.

In some embodiments, the markers that are compared between the protein expression profile of the resected tumor or biopsy sample and the protein expression profile of the melanoma cell lysate are MAGE-antigens. See, for example, Scanlan, Matthew J. et al., Immunological Revs. 2002, 188:22-32 and Weon J L, Potts P R. The MAGE protein family and cancer. *Curr Opin Cell Biol*. 2015; 37:1-8. doi:10.1016/j.ceb.2015.08.002, each of which is incorporated by reference in its entirety.

In some embodiments, the melanoma cell lysate is derived from a cell line selected from the group consisting of DDM-1.7, DDM-1.13, or a combination thereof. In some embodiments, the melanoma cell lysate is the MCV tumor lysate, or one that matches some portion of the MCV tumor lysate expression profile.

In some embodiments, the route of administration is via, intratumoral, peritumoral, intradermal, subcutaneous, intramuscular, intraperitoneal injection. The compositions are administered to stimulate an immune response, and can be given by bolus injection, continuous infusion, sustained release from implants, or other suitable technique.

For the purpose of illustration only, the method can be practiced by obtaining and saving blood samples from the subject prior to infusion for subsequent analysis and comparison. Generally at least about $10^4$ to $10^6$ and typically, between $1\times10^8$ and $1\times10^{10}$ cells are infused intravenously or intraperitoneally into a 70 kg patient over roughly 60-120 minutes.

In some aspects, any of the methods of treatment described herein can further comprise administering one or more additional anti-cancer therapies to the individual. Various classes of anti-cancer agents can be used. Non-limiting examples include: radiation therapy, alkylating agents (e.g. cisplatin, carboplatin, or oxaliplatin), antimetabolites (e.g., azathioprine or mercaptopurine), anthracyclines, plant alkaloids (including, e.g. *vinca* alkaloids (such as, vincristine, vinblastine, vinorelbine, or vindesine) and taxanes (such as, paclitaxel, taxol, or docetaxel)), topoisomerase inhibitors (e.g., camptothecins, irinotecan, topotecan, amsacrine, etoposide, etoposide phosphate, or teniposide), podophyllotoxin (and derivatives thereof, such as etoposide and teniposide), antibodies (e.g., monoclonal or polyclonal), tyrosine kinase inhibitors (e.g., imatinib mesylate (Gleevec® or Glivec®)), hormone treatments, soluble receptors and other antineoplastics (e.g., dactinomycin, doxorubicin, epirubicin, bleomycin, mechlorethamine, cyclophosphamide, chlorambucil, or ifosfamide).

Additionally, in some embodiments, the cells and compositions provided herein can be used adjunctive to, or with, other agents or treatments having anti-cancer properties (See, U.S. Pat. No. 9,914,783, which is hereby incorporated by reference in its entirety). When used adjunctively, the recombinant DCs and related compositions and other agent(s) may be formulated together in a single, combination pharmaceutical formulation, or may be formulated and administered separately, either on a single coordinated dosing regimen or on different dosing regimens. Agents administered adjunctive to or with the recombinant DCs and related compositions will typically have complementary activities to the recombinant DCs and related compositions, such that the cells and other agents do not adversely affect each other.

Agents that may be used adjunctively with anti-PD-1 antibodies include, but are not limited to, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

BiTE antibodies are bispecific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

siRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include, but are not limited to, altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, and trofosfamide.

Angiogenesis inhibitors include, but are not limited to, endothelial-specific receptor tyrosine kinase (Tie-2) inhibitors, epidermal growth factor receptor (EGFR) inhibitors, vascular endothelial growth factor receptor (VEGF) inhibitors, delta-like ligand 4 (DLL4) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, and vascular endothelial growth factor receptor tyrosine kinase (VEGFR) inhibitors.

Antibody drug conjugates include, but are not limited to, those that target c-Met kinase (e.g., ADCs described in U.S. Pat. No. 7,615,529), LRRC15, CD30 (e.g., ADCETRIS® (brentuximab vedotin)), CS1 (e.g., ADCs described in US publication no. 20160122430), DLL3 (e.g., rovalpituzumab tesirine (ROVA-T)), HER2 (e.g., KADCYLA® (trastuzumab emtansine)), EGFR (e.g., ADCs described in US publication no. 20150337042), and prolactin receptor (e.g., ADCs described in US publication no. 20140227294).

Antimetabolites include, but are not limited to, ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-.beta.-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, ribavirin, triapine, trimetrexate, S-1, tiazofurin, tegafur, TS-1, vidarabine, and UFT.

Antivirals include, but are not limited to, ritonavir, acyclovir, cidofovir, ganciclovir, foscarnet, zidovudine, ribavirin, and hydroxychloroquine.

Aurora kinase inhibitors include, but are not limited to, ABT-348, AZD-1152, MLN-8054, VX-680, Aurora A-specific kinase inhibitors, Aurora B-specific kinase inhibitors and pan-Aurora kinase inhibitors.

Bcl-2 protein inhibitors include, but are not limited to, ABT-263 (navitoclax), AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenyl sulfanyl)methyl)propyl) amino)-3-nitrobenzene sulfonamide), N-(4-(4-((2-(4-chlorophenyl)-5,5-dimethyl-1-cyclohex-1-en-1-yl)methyl) piperazin-1-yl)benzoyl)-4-(((1R)-3-(morpholin-4-yl)-1-((phenylsulfanyl)methyl-) propyl)amino)-3-((trifluoromethyl)sulfonyl)benzenesulfonamide, venetoclax and GX-070 (obatoclax).

Bcr-Abl kinase inhibitors include, but are not limited to, DASATINIB® (BMS-354825) and GLEEVEC® (imatinib).

BTK inhibitors include, but are not limited to, ibrutinib and acalabrutinib.

CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC-202, R-roscovitine), abemaciclib, palbociclib. and ZK-304709.

COX-2 inhibitors include, but are not limited to, ABT-963, ARCOXIA® (etoricoxib), BEXTRA® (valdecoxib), BMS347070, CELEBREX® (celecoxib), COX-189 (lumiracoxib), CT-3, DERAIVIAXX® (deracoxib), JTE-522, 4-methyl-2-(3,4-dimethylphenyl)-1-(4-sulfamoylphenyl-1H-pyrrole)-, MK-663 (etoricoxib), NS-398, parecoxib, RS-57067, SC-58125, SD-8381, SVT-2016, S-2474, T-614, and VIOXX® (rofecoxib).

EGFR inhibitors include, but are not limited to, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TAGRISSO® (osimertinib), TP-38, EGFR fusion protein, and TYKERB® (lapatinib).

ErbB2 receptor inhibitors include, but are not limited to, CP-724-714, CI-1033 (canertinib), HERCEPTIN® (trastuzumab), TYKERB® (lapatinib), OMNITARG® (2C4, pertuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, and mAB 2B-1.

Histone deacetylase inhibitors include, but are not limited to, depsipeptide, LAQ-824, MS-275, trapoxin, suberoylanilide hydroxamic acid (SAHA), TSA, and valproic acid.

HSP-90 inhibitors include, but are not limited to, 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090, and VER49009.

Inhibitors of apoptosis proteins include, but are not limited to, HGS1029, GDC-0145, GDC-0152, LCL-161, and LBW-242.

Activators of death receptor pathway include, but are not limited to, TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include, but are not limited to, Eg5 inhibitors such as AZD4877, ARRY-520; and CENPE inhibitors such as GSK923295A.

JAK-2 inhibitors include, but are not limited to, CEP-701 (lesaurtinib), XL019 and INCB018424.

MEK inhibitors include, but are not limited to, ARRY-142886, ARRY-438162, PD-325901, and PD-98059.

mTOR inhibitors include, but are not limited to, AP-23573, CCI-779, everolimus, RAD-001, rapamycin, temsirolimus, ATP-competitive TORC1/TORC2 inhibitors, including PI-103, PP242, PP30, and Torin 1.

Non-steroidal anti-inflammatory drugs include, but are not limited to, AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), and DAYPRO® (oxaprozin).

PDGFR inhibitors include, but are not limited to, C-451, CP-673 and CP-868596.

Platinum chemotherapeutics include, but are not limited to, cisplatin, ELOXATIN® (oxaliplatin) eptaplatin, lobaplatin, nedaplatin, PARAPLATIN® (carboplatin), satraplatin, and picoplatin.

Polo-like kinase inhibitors include, but are not limited to, BI-2536.

Phosphoinositide-3 kinase (PI3K) inhibitors include, but are not limited to, wortmannin, LY294002, XL-147, CAL-120, ONC-21, AEZS-127, ETP-45658, PX-866, GDC-0941, BGT226, BEZ235, and XL765.

Thrombospondin analogs include, but are not limited to, ABT-510, ABT-567, ABT-898, and TSP-1.

VEGFR inhibitors include, but are not limited to, ABT-869, AEE-788, ANGIOZYME™ (a ribozyme that inhibits angiogenesis (Ribozyme Pharmaceuticals (Boulder, Colo.) and Chiron (Emeryville, Calif.)), axitinib (AG-13736), AZD-2171, CP-547,632, CYRAMZA® (ramucirumab), IM-862, MACUGEN® (pegaptamib), NEXAVAR® (sorafenib, BAY43-9006), pazopanib (GW-786034), vatalanib (PTK-787, ZK-222584), SUTENT® (sunitinib, SU-11248), STIVARGA® (regorafenib), VEGF trap, and ZACTIMA™ (vandetanib, ZD-6474).

Antibiotics include, but are not limited to, intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), and zinostatin.

Topoisomerase inhibitors include, but are not limited to, aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, Onivyde™ (liposomal irinotecan), orathecin, pirarubicin, pixantrone, rubitecan, sobuzoxane, SN-38, tafluposide, and topotecan.

Antibodies include, but are not limited to, AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, OX-40 specific antibodies, PANOREX® (edrecolomab), RENCAREX® (WX G250), RITUXAN® (rituximab), ticilimumab, trastuzumab, pertuzumab, VECTIBIX® (panitumumab) and CD20 antibodies types I and II.

Hormonal therapies include, but are not limited to, ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), and ZOLADEX® (fosrelin, goserelin).

Deltoids and retinoids include, but are not limited to, seocalcitol (EB1089, CB1093), lexacalcitrol (KH1060), fenretinide, PANRETIN® (aliretinoin), ATRAGEN® (liposomal tretinoin), TARGRETIN® (bexarotene), and LGD-1550.

PARP inhibitors include, but are not limited to, ABT-888 (veliparib), KU-59436, AZD-2281 (olaparib), AG-014699 (rucaparib), MK4827 (niraparib), BMN-673 (talazoparib), iniparib, BSI-201, BGP-15, INO-1001, and ONO-2231.

Plant alkaloids include, but are not limited to, vincristine, vinblastine, vindesine, and vinorelbine.

Proteasome inhibitors include, but are not limited to, VELCADE® (bortezomib), KYPROLIS® (carfilzomib), MG132, NPI-0052, and PR-171.

Examples of immunologicals include, but are not limited to, interferons, immune checkpoint inhibitors, co-stimulatory agents, and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Immune check point inhibitors include antibodies that target PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Co-stimulatory agents include, but are not limited to, antibodies against CD3, CD40, CD40L, CD27, CD28, CSF1R, CD137 (e.g., urelumab), B7H1, GITR, ICOS, CD80, CD86, OX40, OX40L, CD70, HLA-DR, LIGHT, LIGHT-R, TIM3, A2AR, NKG2A, KIR (e.g., lirilumab), TGF-.beta. (e.g., fresolimumab) and combinations thereof.

Other agents include, but are not limited to, ALFAFERONE® (IFN-.alpha.), BAM-002 (oxidized glutathione), BEROMUN® (tasonermin), BEXXAR® (tositumomab), CAMPATH® (alemtuzumab), dacarbazine, denileukin, epratuzumab, GRANOCYTE® (lenograstim), lentinan, leukocyte alpha interferon, imiquimod, melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZINBRYTA® (daclizumab high-yield process), and ZEVALIN® (.sup.90Y-Ibritumomab tiuxetan).

Biological response modifiers are agents that modify defense mechanisms of living organisms or biological responses, such as survival, growth or differentiation of tissue cells to direct them to have anti-tumor activity and include, but are not limited to, krestin, lentinan, sizofiran, picibanil PF-3512676 (CpG-8954), and ubenimex.

Pyrimidine analogs include, but are not limited to, cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), and TROXATYL™ (triacetyluridine troxacitabine).

Purine analogs include, but are not limited to, LANVIS® (thioguanine) and PURINETHOL® (mercaptopurine).

Antimitotic agents include, but are not limited to, batabulin, epothilone D (KOS-862), N-(2-((4-hydroxyphenyl) amino)pyridin-3-yl)-4-methoxybenzenesulfonamide, ixabepilone (BMS 247550), TAXOL® (paclitaxel), TAXOTERE® (docetaxel), PNU100940 (109881), patupilone, XRP-9881 (larotaxel), vinflunine, and ZK-EPO (synthetic epothilone).

Ubiquitin ligase inhibitors include, but are not limited to, MDM2 inhibitors, such as nutlins, and NEDD8 inhibitors such as MLN4924.

The recombinant DCs and related compositions may also be used to enhance the efficacy of radiation therapy. Examples of radiation therapy include external beam radiation therapy, internal radiation therapy (i.e., brachytherapy) and systemic radiation therapy.

The recombinant DCs and related compositions may be administered adjunctive to or with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, hi strelin, hydroxycarbamide, ibandronic acid, IGN-101, IL-13-PE38, IL-13-PE38QQR (cintredekin besudotox), IL-13-pseudomonas exotoxin, interferon-.alpha., interferon-.gamma., JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-.alpha.), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), and zorubicin, as well as combinations of any of these agents.

Kits

Additionally, certain components or embodiments of these recombinant dendritic cell compositions can be provided in a kit. For example, any of the recombinant dendritic cell compositions, as well as the autologous or other tumor cell lysate compositions can be provided frozen and packaged as a kit, alone or along with separate containers of any of the other agents from the pre-conditioning or post-conditioning steps, and optional instructions for use.

Some embodiments are also directed to any of the aforementioned cellular compositions in a kit. In some embodiments, the kit may comprise ampoules, disposable syringes, capsules, vials, tubes, or the like. In some embodiments, the kit may comprise a single dose container or multiple dose containers comprising the topical formulation of embodiments herein. In some embodiments, each dose container may contain one or more unit doses. In some embodiments, the kit may include an applicator. In some embodiments, the kits include all components needed for the stages of conditioning/treatment. In some embodiments, the cellular compositions may have preservatives or be preservative-free (for example, in a single-use container). In some embodiments, the recombinant dendritic cell compositions expressing any one or more of CD40L, CXCL13, or CD93 may be prepared and frozen in an immature stage, suitable for shipping to a hospital or treatment center. In some embodiments, the antigens for loading, either autologous or for example melanoma cell lysate derived from a cell line such as DDM-1.7, DDM-1.13, or a combination thereof, can be prepared and frozen separately from the recombinant dendritic cell compositions, using standard methods, such that these compositions can be shipped to a hospital or treatment center for further processing and administration to the patient. In yet further embodiments, the recombinant dendritic cell compositions expressing any one or more of CD40L, CXCL13, or CD93 may be prepared and mixed with the desired autologous or for example melanoma cell lysate derived from a cell line such as DDM-1.7, DDM-1.13, to facilitate loading of the recombinant dendritic cells with the tumor antigens, after which this mixture is frozen, such that these compositions can be shipped to a hospital or treatment center for further processing and administration to the patient.

Additionally, in certain patients, it is expected that any of the methods or treatment regimens would be repeated periodically to boost the immune system response to the tumors or infectious agent/s. Such periodic treatment can vary from once every week, month, to once every two months, to once every 3 months, to once every 4 months, to once every 5 months, to once every 6 months, or once every 7 months, or once every 8 months, or once every 9 months, or once every 10 months, or every 11 months, or once annually as a maintenance treatment for as long as the patient requires.

Outline of Treatments

In some embodiments, alloDCs are transduced with CD40L and CXCL13 in order to maximize the attraction of patients' T cells and B cells, and generate the cascade of anti-tumor cellular and humoral immune response.

In optional further embodiments, transduction of the CD40L+ and CXCL13+ alloDCs with CD93 further facilitates the cross-talk between the allogeneic DCs and the host DCs, creating a stable and sustained host anti-tumor immunogenicity.

In patients whose tumors are able to be biopsied or resected, the protein expression profile of the resected tumor samples and biopsy samples are screened. If the expression profiling indicates at least 3 fragments shared with GMP-MCV, then the recombinant imDC is loaded with GMP-MCV (an allogenic, or "off the shelf" tumor lysate) before the DCs are matured in vitro.

For patients whose samples lack any shared tumor fragments with allogeneic/off the shelf lystates, autologous tumor lysate is generated and the tumor lysate presented to the immature recombinant alloDCs for the autologous tumor lysate to be processed and presented by the recombinant immature alloDcs.

For any non-resectable and non-biopsyable patient, the recombinant CD40L+CXC13+ alloDC (or optionally further including CD93+) cell composition will be administered to the patient without antigen loading as an immune adjuvant. Using this CD40L+CXCL13+(optional) CD93 AlloDC approach, late stage cancer patients can mount new antitumor cellular and humoral immune response to tumor neoantigens and strengthen the existing immune response with prompt, efficient and low-cost therapy.

A Summary of these Options is Described Below:

Option 1: The protein expression profile of the resected tumor samples and biopsy samples are screened for cross-matching with the MelCancerVac (MCV) tumor lysate expression profile. If the expression profiling indicates at least 3 same fragments with the GMP-MCV tumor lysate, the off-the-shelf product, MCV tumor lysate pulsed enhanced/activated recombinant allogeneic DC vaccine (alloDC/MCV tumor lysate) can be used for the patient.

Option 2: If the protein expression profile doesn't match the profile of MCV lysate, autologous tumor lysate is presented to immature recombinant alloDCs, to be matured after the pulsing in vitro.

Option 3: For non-resectable and non-biopsy patients, CD40L+CXCL13 (and optionally CD93) recombinant alloDC can be administered as an immune adjuvant without antigen pulsing or activation.

An option for making the recombinant DC cells is to use recombinant adenoviral vector/CRISPR Cas9 to transduce the CD40L and CXCL13 into the purified human CD14+ monocytes rather than lentiviral vector or retroviral vector. Transduction efficiency and the functionality of the transduced monocytes will be evaluated, including migration, differentiation, and cytokine secretion to ensure the recombinant/transgenic monocytes can be differentiated into functional and immunogenic DCs.

Using adenoviruses (AdV) is beneficial for a number of reasons, including having high transduction efficiency for many cell types including cells of hematopoietic origin independent of their mitotic status. Another benefit is that replication-defective AdV have demonstrated a safety profile clinically. Furthermore, AdV provide a high level of transgene expression, and AdV-transduced DCs can effectively present antigenic proteins. Recombinant adenoviral vectors can successfully transfect immature DCs to 95% efficiency. (See: Lei Zhong, et al. Eur. J. Immunol. 1999.29: 964-972.) However, it is also expected that additional viral vector systems could be utilized including lentiviral vectors. (See, commercial sources such as Vectalys (Toulouse France) and related methods in U.S. Pat. No. 10,272,111).

Chemokine (C—X—C motif) ligand 13 (CXCL13), also known as B lymphocyte chemoattractant (BLC) or B cell-attracting chemokine 1 (BCA-1), is a protein ligand that in humans is encoded by the CXCL13 gene. CXCR5 is the receptor for CXCL13. Chemokines expression starts a positive loop of recruitment and stimulation of lymphocytes. Overexpressing CXCL13 in intestinal epithelial cells promoted a marked increase in the number of B cells in the lamina propria and an increase in the size and number of lymphoid follicles in the small intestine. (See, F. Marchesi et al. Mucosal Immunology. 2009. 2(6):486-494.)

These results suggest that overexpression of CXCL13 in the intestine during inflammatory conditions favors mobilization of B cells and of LTi and NK cells with immunomodulatory and reparative functions.

CD40 ligand (CD40L), also called CD154, is a protein that is a member of the TNF superfamily of molecules. It binds to CD40 on antigen-presenting cells (APC), which leads to many effects depending on the target cell type. In total CD40L has three binding partners: CD40, α5β1 integrin and αIIbβ3. CD154 acts as a costimulatory molecule and is particularly important on a subset of T cells called T follicular helper cells (TFH cells). On TFH cells, CD40L promotes B cell maturation and function by engaging CD40 on the B cell surface and therefore facilitating cell-cell communication. CD40L stable expression allows DCs to produce IL-12 to overcome immunosuppression and to trigger memory T cell differentiation.

CD93 is an approximately 120 kDa O-sialoglycoprotein that within the hematopoietic system is selectively expressed on cells of the myeloid lineage. Its primary structure and function were unknown until recently. Retroviral-expression cloning was utilized to isolate the CD93 cDNA. Sequence analysis revealed that CD93 is identical to a protein on human phagocytes termed C1q receptor (C1qRp). C1qRp was shown previously to mediate enhancement of phagocytosis in monocytes and was suggested to be a receptor of C1q and two other structurally related molecules. When studying CD93 transductants and control cells, it was found that cells expressing CD93 have enhanced capacity to bind C1q. Furthermore, it was shown that immature dendritic cells (DC) express CD93/C1qRp, and mature DC, known to have reduced capacity for antigen uptake and to have lost the ability to phagocytose, show weak-to-negative CD93/C1qRp expression.

The cells that are used as the source of the cells for transduction with the heterologous proteins provided herein can be any donor. In some embodiments, the donor is screened to establish that the cells isolated from the donor would be considered allogeneic to the subject to which they are administered. In some embodiments, the donor screening criteria can include donor demographics including: donor age, donor gender, donor ethnicity, donor ABO/Rh; donor BMI (weight and height), donor HLA high resolution typing.

Additionally, in some embodiments, donor samples can have a full panel testing for blood transfusion (FDA), on leukopheresis material (or whatever the source material is) including: CMV test; serological testing for syphilis and an antibody screen; and infectious disease panel comprising one or more of the following tests: Hepatitis B Core Antibody (Anti-HBs EIA); Hepatitis B Surface Antigen (HBsAg EIA); Hepatitis C Virus Antibody (Anti-HCV EIA); Human Immunodificiency Virus Ab (HIV1/2 plus O); Human T-lymphotropic Virus Antibody (HTLV-I/II); HIV-1/HGV/HBV nucleic Acid testing; WNV Nucleic Acid Testing; *Trypanasoma cruzi* Antibody; and Zika. Thus, in some embodiments, the donor cells or the cells that are administered to the patient are derived from a donor that is free of CMV, syphilis, Hepatitis A, Hepatitis B, Hepatitis C, HIV, HTLV-I/II, West Nile Virus (WNV), *Trypanasoma cruzi*, and/or Zika.

The samples may be evaluated for monocyte percentages and count by hematology analyzer and flow cytometry.

The samples may be collected by apheresis or by whole blood collection and subject to standard inspection. In certain instances, the collection will be by Optia leukopheresis collection. The samples will be analyzed for viability and CD14+% and the CD14+ monocytes will be counted.

It is another option to conduct monocyte negative isolation using CliniMACS according to standard procedures. Post Isolation Purity and Cell Count In some embodiments, transfect purified monocyte with adenoviral vector comprising CD40L and CXCL13 (and for certain embodiments CD40L, CXCL13, and CD93).

In some embodiments, transfect purified monocyte with lentiviral vector comprising CD40L and CXCL13 (and for certain embodiments CD40L, CXCL13, and CD93).

After exposure to the viral vector, the positively transduced monocytes can be selected. For example, the cells can be selected with one or more of the following positive or negative markers: Linage negative (CD3−, CD56−, CD19−, CD66b−), CD45+, CD14+, CD40L+, CXCL13+, CD1c+, CD11b+, CD11c+, HLA-DR+, CD86+, CD80low, CD83−, CD16Low, CD33+, CD163−, CD206+, or CD209.

In certain instances the transduction efficiency of cells will be evaluated, prior to positive sorting so that yield can be calculated. Transduction efficiency is required/useful to determine the expected yield of CD40L+CXCL13+ or CD40L+CXCL13+CD93+ monocyte cells.

As provided herein, the cells can be monocytes can be differentiated into immature dendritic cells in vitro. In some embodiments, the cells (transduced or non-transduced) are centrifuge to isolate the cells. The cells can be, for example, centrifuged at 400×g for 10 minutes at room temperature (RT) with low break. The centrifuged cells can be separated from their supernatant. The centrifuged cells can be resuspended with X-VIVO 15, recombinant human GM-CSF, such as (1000 Unit/ml) and IL-4 (1000 Unit/ml) in cell culture flask, and the cells can be allowed to differentiate the monocytes in incubator for at least or about 1, 2, 3, 4, 5, 6, 7, 8, 9, or 10 days. In some embodiments, the cells are allowed to differentiate for about 4 to about 8 days.

In some embodiments, the differentiated cells, can then be collected from the cell culture media and centrifuged. For example, in some embodiments, the cell culture media is collected from the culture flasks into centrifuge tubes. PBS can be placed into cell culture flasks to cover the surface of the flasks. The cell culture flask can be incubated with PBS at 37° C., 5% $CO_2$ incubator for about 30 minutes. In some embodiments, the contents of the flasks are collected into the centrifuge tubes by tapping the flasks after incubation. The flasks can be rinsed and collected into centrifugation tubes. In some embodiments, the collected cells can be centrifuged, for example, at 400×g for 10 minutes at RT with low break. After centrifugation, the cells are separated from their supernatant and the cells are isolated. The cells can be re-suspend and analyzed for viability.

In some embodiments, the samples are analyzed for count and flow cytometry identification of related biomarkers. They can be analyzed by or can be selected with one or more of the following positive or negative markers: Linage negative (CD3−, CD56−, CD19−, CD66b−), CD45+, CD14+, CD40L+, CXCL13+, CD1c+, CD11b+, CD11c+, HLA-DR+, CD86+, CD80low, CD83−, CD16Low, CD33+, CD163−, CD206+, or CD209.

As provided herein, the monocytes can be transduced with a viral vector, such as a lentivirus or an adenovirus. Any protocol for viral transduction can be used. For example, the cells can be cultured in a media cocktail. In some embodiments, the media comprises 100 ng/mL of mFlt3L/mTPO/mSCF, and 30 ng/mL of mIL-3. The cells can, for example, be cultured in this media incubate at 37° C. and 5% $CO_2$ for 24 hours or until activated. Following activation, the cells can be pre-treated with PGE2. The cells can then be transduced with the appropriate vector. In some embodiments, the virus is added at a MOI (multiplicity of infection) of 10, 100, or 100. After transductions, the cells can be isolated using, for example, beads or purification products that bind to one or more of the heterologous proteins encoded for by the vector. For example, cells can be collected after the transduction process using CD40L microbeads (Miltenyi) to purify the cells expressing the CD40L.

In some embodiments, to differentiate the transduced monocytes, such as CD34+ Lentivirus+-transduced cells into CD14+CD16+ monocytes, the purified CD34+Lv+ cells can be expanded for 3-10 days by culturing 1×10$^5$ CD34$^+$ cells/ml in the expansion media in a G-Rex 10M (X-VIVO 10 media; Human AB serum 10%; rhSCF 50 ng/ml (R&D Systems); TPO 15 ng/ml (R&D Systems); IL-3 30 ng/ml (R&D Systems); Flt-3L 30 ng/ml (R&D Systems). After expansion of the cells (1-10 days), the cells can be moved into the differentiation medium in a G-Rex 100M for 14 days. One non-limiting example of differentiation medium includes, but is not limited to, IMDM with 20% of Human AB serum; SCF 25 ng/ml (R&D Systems); M-CSF 30 ng/ml (R&D Systems); IL-3 30 ng/ml (R&D Systems); and Flt-3L 30 ng/ml (R&D Systems). The cells can then be incubated in a differentiation cocktail for about, or at least 1, 2, 3, 4, 5, 6, 7, 8, 9, or 10 days. A non-limiting example of a differentiation cocktail is RPMI-1640; 3% Human AB serum; GM-CSF 900 IU/ml; IL-4 1000 IU/ml; TNF alpha 400 IU/ml; and TGF beta1 0.2 ng/ml. The differentiation cocktail can enhance the differentiation of the monocytes into immature dendritic cells.

In some embodiments, to further enhance the maturation of the immature dendritic cells, the cells can be incubated in a maturation cocktail. In some embodiments, the maturation cocktail comprises an antigen, a tumor lysate or a live tumor cell. Examples of these are provided herein. The maturation cocktail can include, for example, GM-CSF 500 IU/ml; IL-15 400 ng/n1; IFN gamma 100 ng/ml; TNF alpha 2 ng/ml; and PgE2 2 mcg/ml. The amounts are exemplary only and are not limited to such amounts. Therefore, in some embodiments, the maturation composition (cocktail) comprises GM-CSF, IL-15, IFN gamma, TNF alapha, and/or PgE2. The cells can incubated in this maturation compositions for about 12 to about 48 hours, about 20 to about 40 hours, about 30 to about 38 hours, about, or at least, 12, 16, 18, 20, 24, 28, 32, 36, 40, 44, or 48 hours. The maturation cocktail can also comprise TNF-$\alpha$, IL-1$\beta$, IFN-$\alpha$, IFN-$\gamma$, and/or pIC.

The results for an experiment using one or more of these embodiments are illustrated in FIGS. 2A-F, a representative phenotyping and purity evaluation using CliniMACS isolated CD14+ monocytes.

Figure 4A:
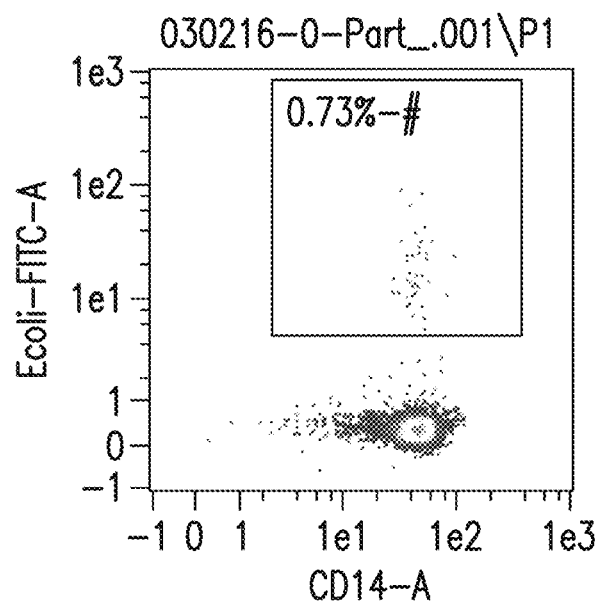
FIGS. 4A-B are flow cytometric images showing that immature recombinant alloDCs exhibit phagocytotic ability.
Figure 4B:
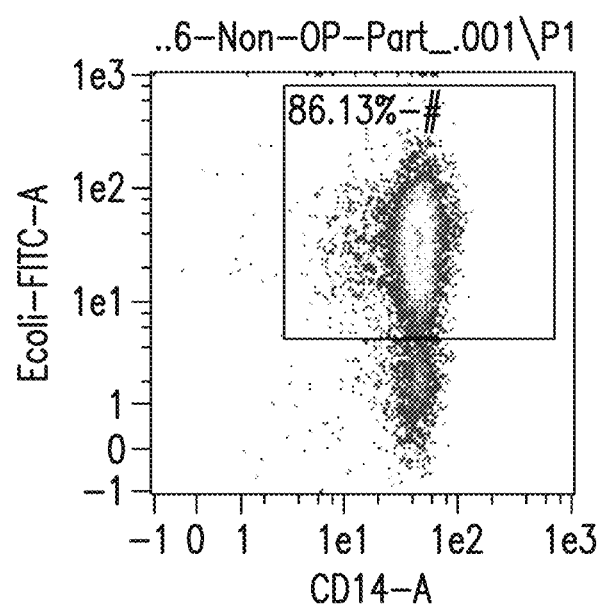

The immature recombinant DCs were shown to exhibit phagocytotic ability illustrated in FIGS. 4A-B. For the results shown in FIGS. 4A-B. the phagocytosis of fluorescently labeled *Escherichia coli* (*E. coli*) particles by the immature DC product was observed by flow cytometry. FIG. 4A is the negative control; while FIG. 4B shows 86.13% of the product had phagocytosed the fluorescently labeled *E. coli* particles. The assays used can be any phagocytotic assay.

Figure 5A:
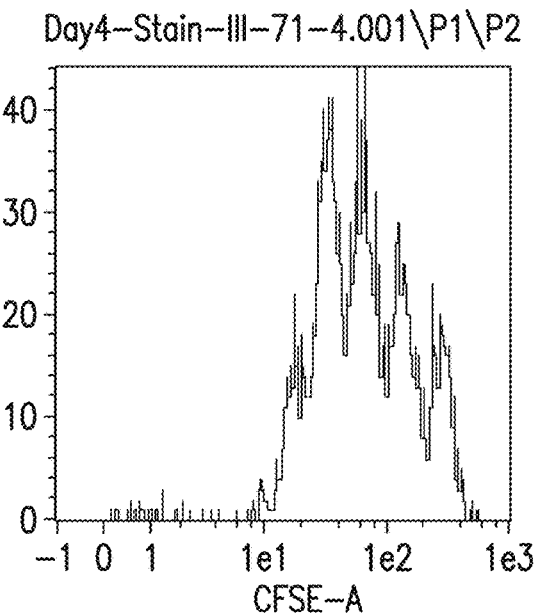
FIGS. 5A-D are images of fluorescent indicators of alloDC stimulated allogenic T-cell proliferation shown by the dilution of carboxyfluorescein succinimidyl ester (CFSE) staining.
Figure 5B:
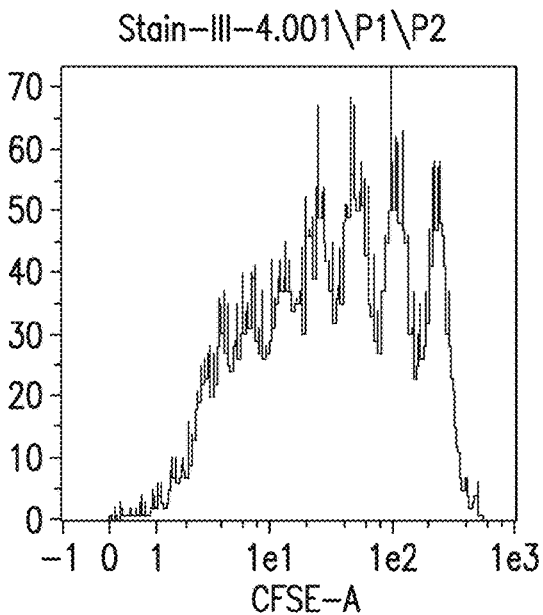
Figure 5C:
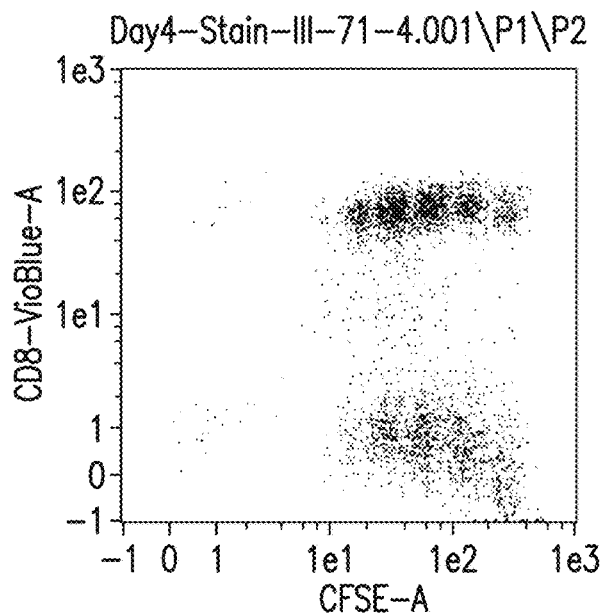
Figure 5D:
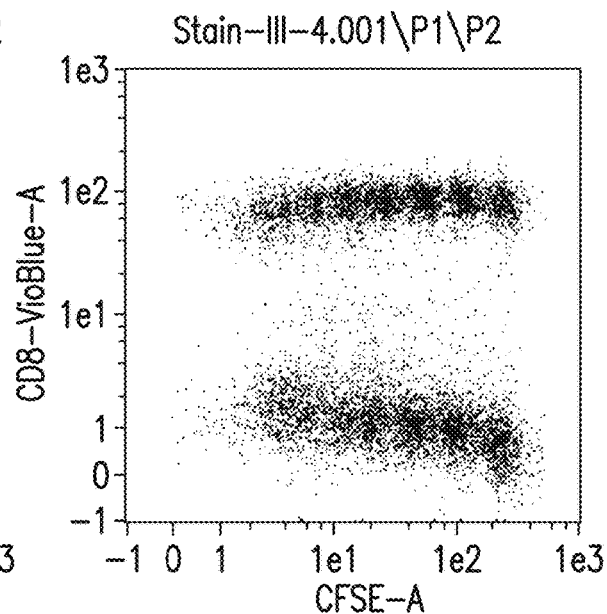

Additionally, FIGS. 5A-D show that the recombinant DCs stimulated allogeneic T cell proliferation as indicated by the dilution of carboxyfluorescein succinimidyl ester (CFSE). For the results shown in FIGS. 5A-D, the allogeneic T cells were labeled with CFSE and co-cultured with recombinant alloDCs. The proliferation of the T cells can be observed by the dilution of CF SE. The left column (FIGS. 5A and C) showed the proliferation on Day 4, and the right column showed the proliferation on Day 7 (FIGS. 5B and D). These results illustrate that recombinant alloDCs stimulated allogeneic T-cell proliferation.

A useful aspect of the present compositions and methods includes the ability to bank the recombinant DCs to provide an off-the shelf vaccine for use at a local hospital, for ease of treating the patient. Such recombinant DCs, could then be handled in three different ways: 1) they could be loaded with autologous tumor lysate, or (2) in other instances they could be loaded with MCV tumor lysate (the Dandrit GMP, if ≥3 epitopes of the patient's tumor is present in the MCV antigen pool), or another commercially available allogeneic tumor lysate; or (3) there could be no antigen loading in the case of non-resectable tumors.

In the next step of recombinant DC vaccine preparation, the recombinant alloDCs are matured with a cocktail of recombinant human cytokines such as those described above.

Figure 9:
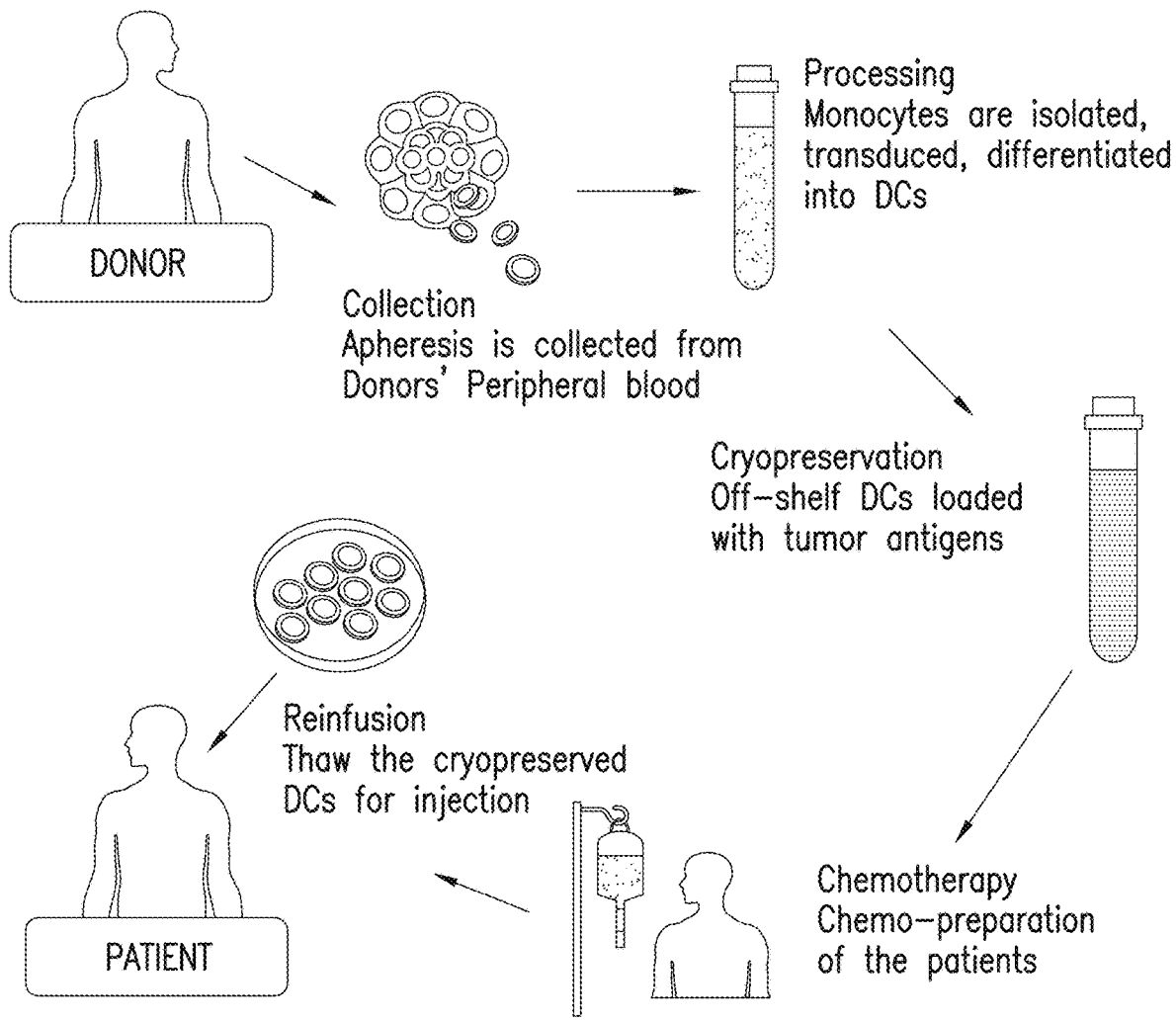
FIG. 9 is a schematic showing an exemplary overview for administering the recombinant alloDC vaccine described herein.

Then the cells are phenotypes and functionally evaluated (as shown in FIGS. 4-5), as well as to be evaluated for the expression of the relevant transgenes (e.g. CD40L, CXCL13, and CD93). Finally, the recombinant DCs are frozen or more specifically, cryopreserved, typically in a controlled rate cryopreservation and then utilized in a clinical setting after thawing. Such cells serve as the basis for the recombinant DC biological vaccine/immune adjuvant for treating cancers, tumors, and malignancies. A schematic of the treatment, cell preparation, and vaccination process is shown in FIG. 9.

In some embodiments, the cells are frozen, which can be referred to as cryopreservation. The cells can, for example, be frozen using CryoStor CS5 (freeze media). However, this is a non-limiting example of freezing media and other freezing media can be used. The cells can be initially chilled 4° C. Then the cells can be further cooled to about −20 C. The cells can be centrifuged or resuspended in additional freeze media and then cooled to −90 C in a stepwise manner. The cells can then be stored in liquid nitrogen. In some embodiments, the cells are frozen in a cryobag.

The cells can be thawed by thawing in a 37° C. water bath. In some embodiments, the cells are thawed without moving the cells in the water bath, that is no FIG. 8 motion or flicking. The cells can then be contacted with plasma and warmed thawing media. The cells can then be analyzed for viability before being administered to the subject. Examples of the markers are provided herein and above.

In some embodiments, the dendritic cells are matured with a cytokine cocktail and/or load the DC with autologous tumor lysate/MCV. For example, the viable immature DCs can be cultured with tumor lysate or MCV with the DC cells. This can be done in the presence of a maturation cocktail, such as described above, or, for example, a composition that comprises TNF-$\alpha$, IL-1$\beta$, IFN-$\alpha$, IFN-$\gamma$, and pIC. The cells can be incubated with this composition for about 12 to about 36 hours, such as, or about, or at least, 20, 22, 24, 26, 28, or 30 hours. The mature cells can then be collected and analyzed. The mature cells can also be frozen using freezing media and stepwise freezing process, such as described herein.

As described herein, the cells can be incubated or loaded with a tumor lysate. The tumor lysate can be prepared in any manner. For example, in some embodiments, the tumor material is provided (isolated, obtained, resected, etc). The sample can be flash frozen in liquid nitrogen. In some embodiment, the sample is free of non-malignant tissue. This can be mean that the sample was removed without any non-malignant tissue or that the sample has been further processed to remove such non-malignant tissue. The sample can then be thawed and flash frozen 1-5 times to help lyse the cells. The lysate can be centrifuged and filtered to prepare the tumor lysate. The lysate can be stored frozen, for example, at −80° C.-freezer.

The embodiments are now described with reference to the following examples. These examples are provided for the purpose of illustration only and the embodiments should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1

Unresectable Patient with Metastatic Colorectal Cancer

Figure 6A:
FIGS. 6A-B are images of a patient's colorectal tumor, before (FIG. 6A) and six months after treatment (FIG. 6B) with autologous tumor loaded alloDC CD40L+ vaccine.
Figure 6B:
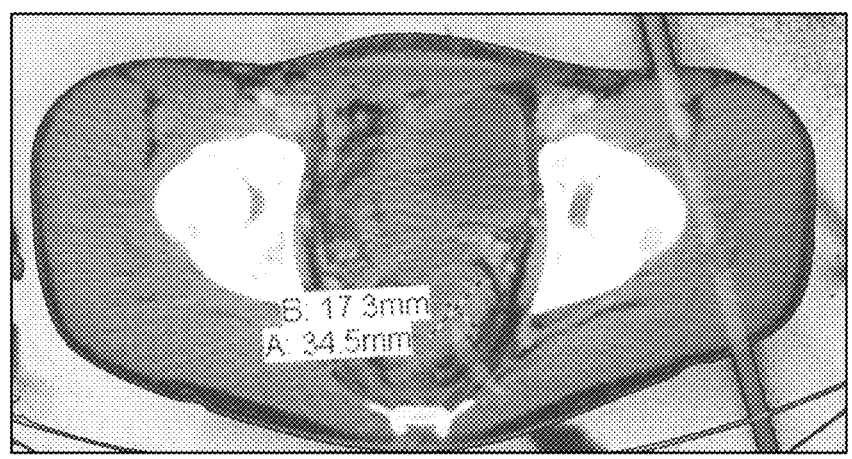
Figure 7A:
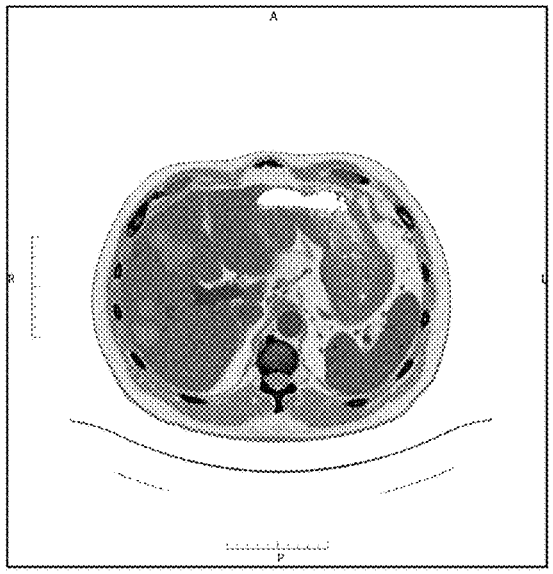
FIGS. 7A-D are images of a patient's multiple liver metastases from an colorectal tumor, before (FIG. 7A, FIG. 7C) and six months after treatment (FIG. 7B and FIG. 7D) with autologous tumor loaded alloDC CD40L+ vaccine.
Figure 7B:
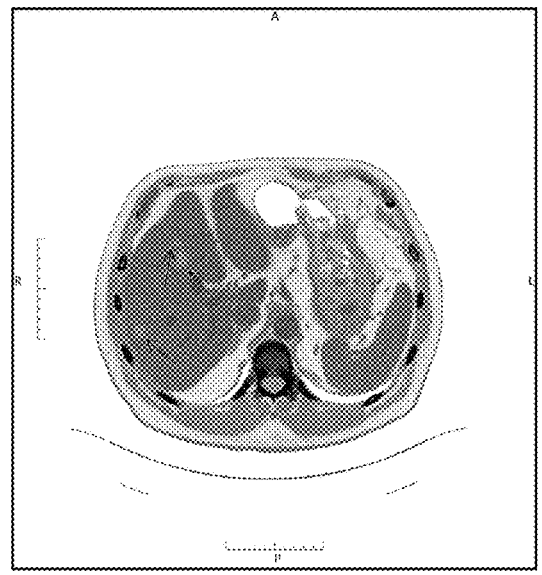
Figure 7C:
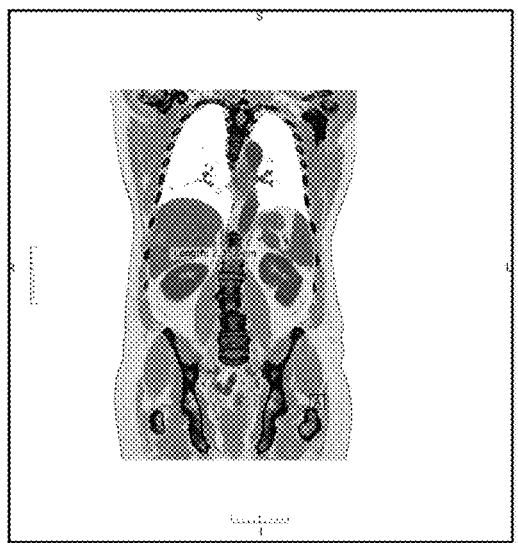
Figure 7D:
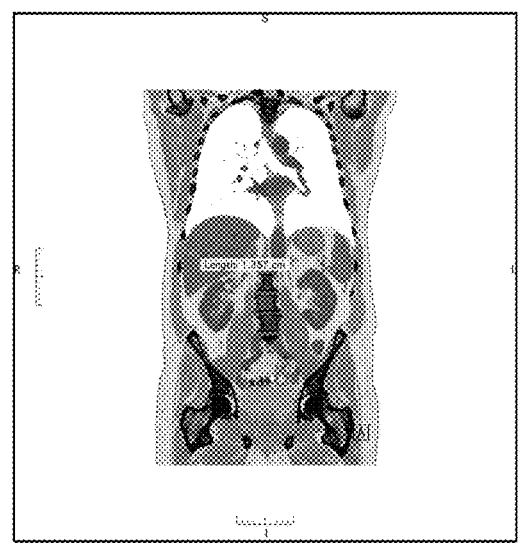
Figure 8A:
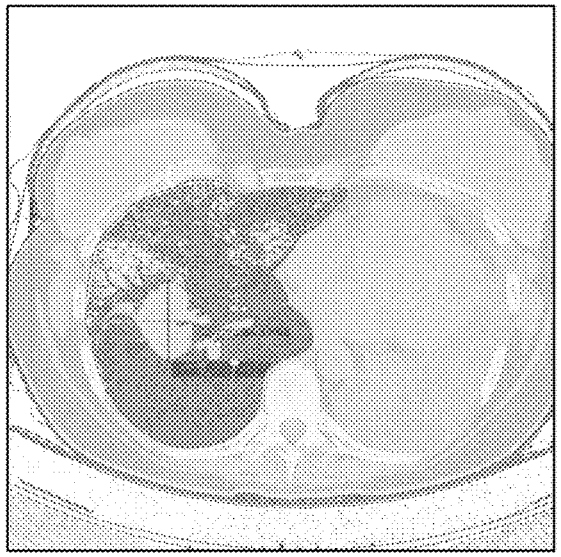
FIGS. 8A-D are images of a patient's metastatic invasive ductal breast tumors, before (FIG. 8A, FIG. 8C) and six months after treatment (FIG. 8B and FIG. 8D) with autologous tumor loaded alloDC CD40L+CXCL13+ vaccine.
Figure 8B:
Figure 8C:
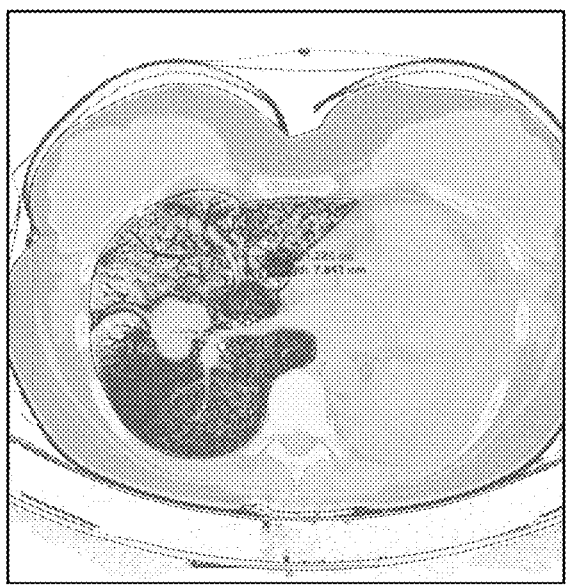
Figure 8D:

A male patient was diagnosed with colorectal cancer at age 29 had a 6 cm primary colorectal tumor removed upon diagnosis. The patient opted out of adjuvant chemotherapy. The patient presented with relapse in primary tumor lesion with multiple mesenteric and hepatic metastases 18 months after the initial surgery. The patient underwent emergency colostomy surgery due the primary tumor relapse (16 cm)

obstructing the colorectal passage. A core biopsy was taken from the patient's primary tumor during the colostomy surgery. Three weeks after the surgery, the patient started receiving allogeneic DCs pulsed with autologous tumor cells presenting CD40L, matured with maturation cocktail, as described herein above. The patient received no other treatments. The vaccine dose schedule was $1 \times 10^6$ Allo-DC CD40L+ loaded cells injected subcutaneously every 15 days. FIGS. 6A-B are CAT/PET scan (CT) images showing significant reduction in the tumor mass 6 months (12 injections) following the Allo-DC CD40L+ loaded cell treatment. The primary tumor shrunk from 12 cm to 17.3 mm×34.5 mm (FIG. 6B) following 6 months of treatment with alloDC CD40L+ vaccine loaded with autologous tumor cells. These cells were transduced to express CD40L, and it is expected that the alloDC cells further transduced with CXCL13 and optionally, CD93 will further augment the anti-tumor effects (loaded with autologous tumor), along the lines of the alloDC CD40L+ cells.

Example 2: 69 Year Old Male with Unresectable Metastatic Colorectal Cancer

A male patient was diagnosed with colorectal cancer at 68 years old. A five centimeter (5 cm) primary colorectal tumor was removed upon diagnosis. The patient received 6 months of FOLFOX regimen. At follow up assessment after FOLFOX treatment, the patient presented with relapse in primary tumor lesion with multiple hepatic and pulmonary metastases. After the follow up, the patient was started on a FOLFIRINOX regimen. Six months into the FOLFIRINOX treatment, the patient underwent emergency colostomy surgery due the primary tumor relapse obstructing the colorectal passage. The patient started receiving autologous tumor pulsed alloDC vaccine presenting CD40L, matured with maturation cocktail, as described herein above.

The patient only received capecitabine during the vaccine treatment. The vaccine dose schedule was $2 \times 10^6$ cells injected subcutaneously every 15 days. The CT/PET images in FIGS. 7A-D show significant reduction in the hepatic and pulmonary masses six months (12 injections) following the alloDC CD40L+ vaccine loaded with autologous tumor cell treatment. These cells were transduced to express CD40L, and it is expected that the alloDC cells further transduced with CXCL13 and optionally, CD93 will further augment the anti-tumor effects (loaded with autologous tumor), along the lines of the alloDC CD40L+ cells.

Example 3: 45 Year Old Female with Metastatic Invasive Ductal Breast Cancer

A female patient diagnosed with HER-2 positive, ER and PR negative breast cancer, and had mastectomy in 2008 (T1cN2M0). The patient received TAC for 6 months and went in remission. In 2010 PET revealed evidence of metastasis. The patient received Gemcitabine, Carboplatin, Trastuuzmab and progressed. Then the patient received bortezomib and lapatinib and the disease still progressed. Third line treatment with ado-trastuzumab emtansine started in 2013 until 2015. Progression in the lungs continued.

The patient next received fifth line treatment with trastuzumab and vinorelbine starting August 2015 and discontinued in April 2016 due to progression. Sixth line treatment with trastuzumab, bortezomib and eribulin started in April 2016 and was discontinued in July 2016 due to progression. Seventh line treatment started with ado-trastuzumab emtansine and pablociclib in July 2017, and was discontinued in January 2018 due to progression. Eighth line treatment with fulvestrant, trastuzumab, and pablociclib was given from January to August 2017, and stopped due to progression.

The patient was diagnosed with brain metastasis in October 2017 with right craniotomy and 5 total brain lesions were treated with stereotactic radiosurgery. The patient had not received any more brain treatment at that time. The patient was started on trastuzumab, ixabepilone and capecitabine in February 2018 and discontinued the treatment in April 2018 due to progression. The patient received whole brain radiation in August 2018 to be physically fit travel to receive the immunotherapy treatments. The patient received adoptive cell therapy as an initial treatment before her bronchoscopic tumor biopsy procedure in September 2018.

The patient started receiving autologous tumor cell pulsed CD40L and CXCL13 expressing alloDCs matured with maturation cocktail, as described herein, in September 2018. The vaccination dose was $10^6$ cells injected subcutaneously (sub-Q). The vaccine schedule was as follows: injections #1-#4 every 7 days, #5-#8 every 10 days, #9-#12 every 15 days (total of 12 sub-Q injections in 130 days). The CT and PET/CT images in FIGS. 8A-D show significant reduction in pulmonary lesions a month following treatment with autologous tumor cell pulsed alloDC CD40L+CXCL13+ cells.

These cells were transduced to express CD40L and CXCL13, and it is expected that the alloDC cells further transduced with CD93 will further augment the anti-tumor effects (loaded with autologous tumor), along the lines of the alloDC CD40L+CXCL13+ cells, in view of the synergistic in vitro results as shown below in FIGS. 10-12.

Example 4: In Vitro Testing

Figure 10:
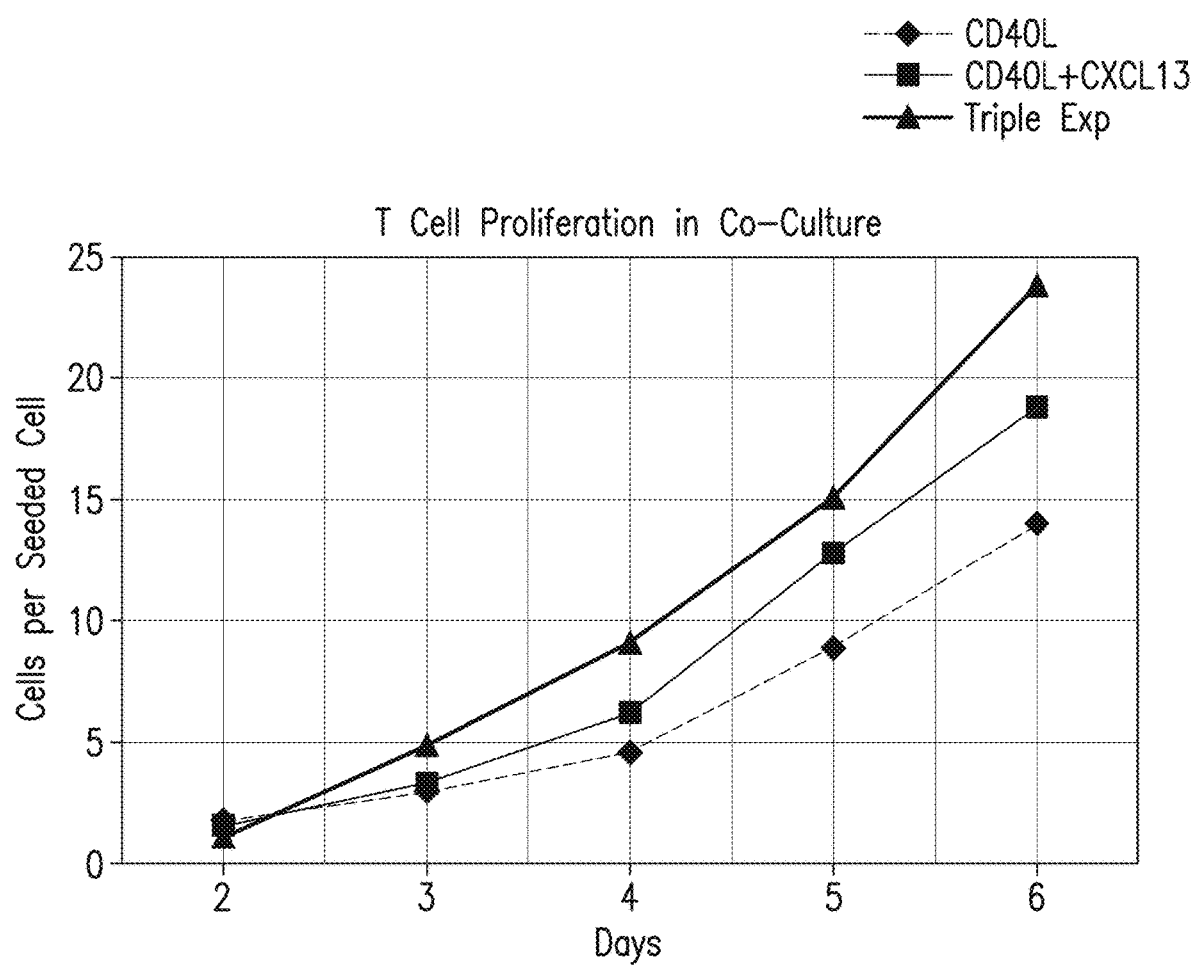
FIG. 10 is a graph showing T cell proliferation in co-culture for recombinant DCs expressing CD40L, CD40L+ CXCL13, or Triple expression of CD40L+CXCL13+CD93, with the triple expression showing the greatest amount of T cell proliferation.

T Cell Proliferation (FIG. 10)

Tumor lysate obtained from a breast cancer patient is used to produce gene-modified mature DCs using a lentivirus expressing CD40L+CXCL13+CD93, or CD40L+CXCL13, or just CD40L. Mature allo-DCs ($2 \times 10^4$) are then co-cultured peripheral blood CD3+ T cells ($1 \times 10^6$) in Tex-MACS (Miltenyi) media supplemented with 500 IU/ml IL-2 (R&D Systems) in triplicates. The persistence of allo-DCs were measured by flow cytometry (CD86 and CD1a) 48h after the seeding. In each condition there were no viable allo-DCs detected at 48h of the co-culture.

Figure 11:
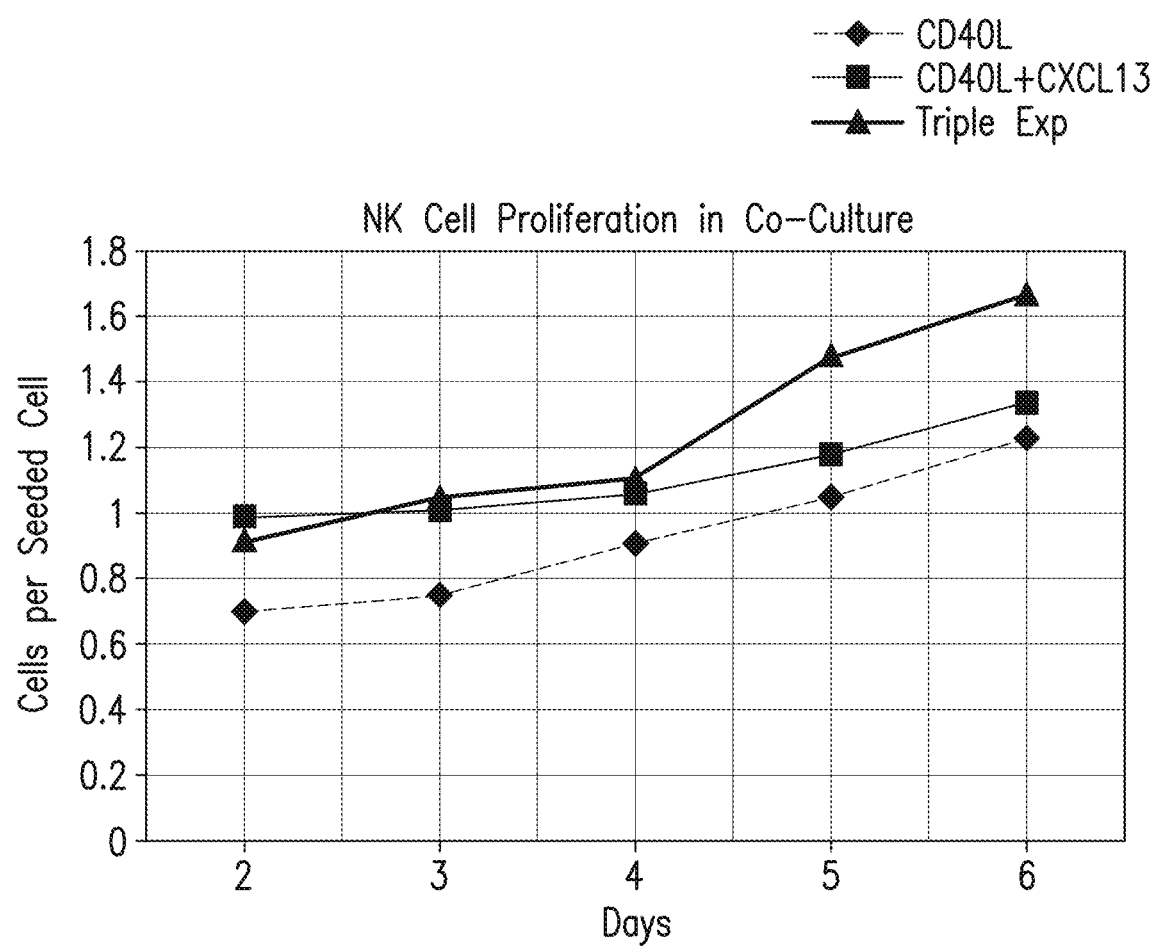
FIG. 11 is a graph showing NK cell proliferation in co-culture for recombinant DCs expressing CD40L, CD40L+ CXCL13, or Triple expression of CD40L+ CXCL13+CD93, with the triple expression showing the greatest amount of NK cell proliferation.

NK Cell Proliferation (FIG. 11)

Tumor lysate obtained from a breast cancer patient is used to produce gene-modified mature DCs using a lentivirus expressing CD40L+CXCL13+CD93, or CD40L+CXCL13, or just CD40L. Mature allo-DCs ($1 \times 10^4$) are then co-cultured peripheral blood CD16+CD56+NK cells ($5 \times 10^5$) in NK Cell media (Miltenyi) with the presence of 500 IU/ml IL2 in triplicates. The persistence of allo-DCs were measured by flow cytometry (CD86 and CD1a) 48h after the seeding. In each condition there were no viable allo-DCs detected at 48h of the co-culture.

Figure 12:
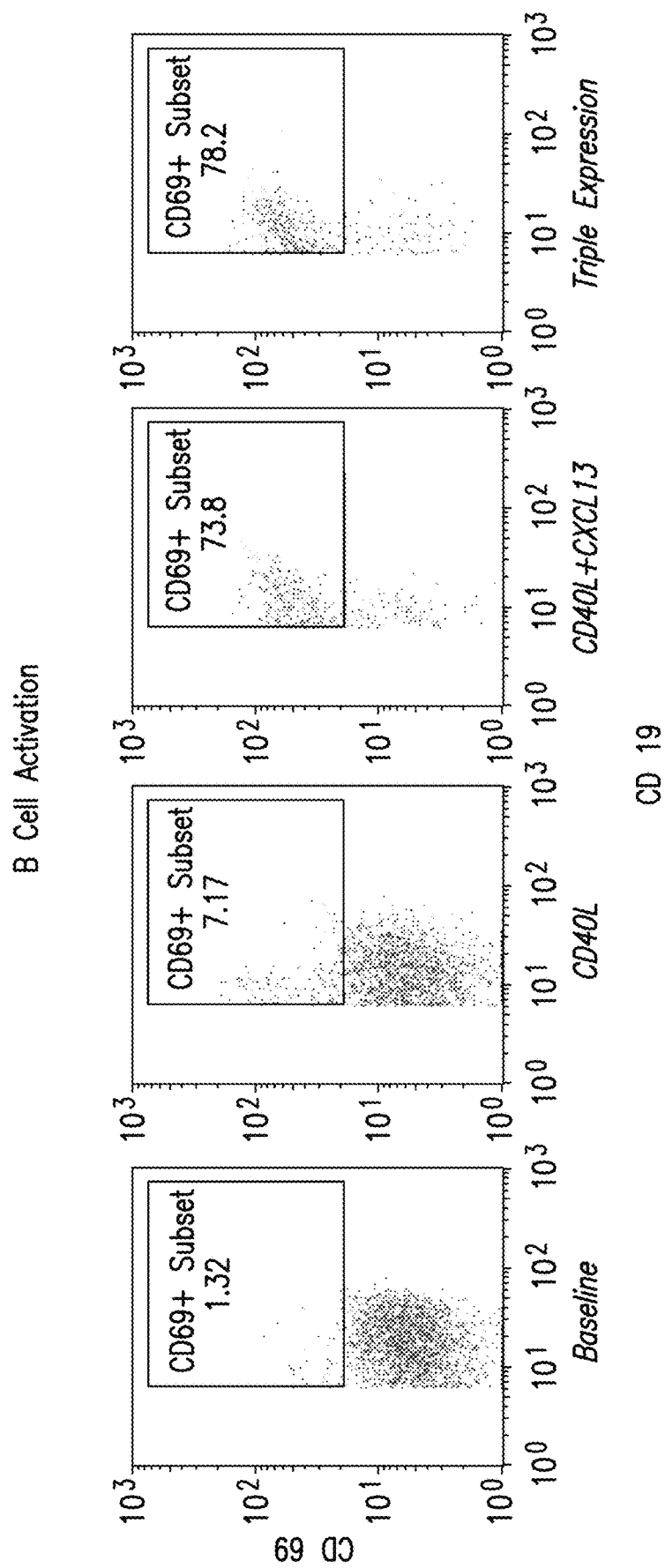
FIG. 12 are cell sorting images for determining B cell activation by determining by flow cytometry the CD69 expression levels in CD19+ cells on day 4.

B Cell Activation (FIG. 12)

Tumor lysate obtained from a breast cancer patient is used to produce gene-modified mature DCs using a lentivirus expressing CD40L+CXCL13+CD93, or CD40L+CXCL13, or just CD40L. Mature allo-DCs ($1 \times 10^4$) are then co-cultured peripheral blood CD19+ B cells ($2.5 \times 10^5$) in RPMI 1640 media with %5 Human AB serum and 1 mM glutamax in triplicates. The activation level of B cells was by flow cytometry by determining the CD69 expression levels in CD19+ cells on day 4.

The results from FIGS. 10-12 show the synergistic effects of co-expressing all three receptors on the recombinant DCs. In FIG. 10, T-cell proliferation was used as a surrogate for indicating increased cellular immune response to the recombinant DCs. The greatest increase in T-cell proliferation was shown for the triple recombinant DC (CD40L+CXCL13+, and CD93). Likewise, in FIG. 11, NK (natural killer) cell proliferation in co-culture with the recombinant DCs was used as another surrogate for increased cellular immune response in vivo. Similarly, in FIG. 11, the greatest increase in NK cell proliferation was shown for co-culture with the triple construct. Finally, in FIG. 12, the activation level of B cells in co-culture was utilized as a surrogate for in vivo B cell activation. B cell activation was determined by analyzing the co-cultured cells for CD69 expression in CD19+ cells on day 4. In these co-cultures, the triple recombinant DC (CD40L+CXCL13+, and CD93) also exhibited the highest level of CD69+ expression, indicating analogously, activation of the humoral immune system.

Standard Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A dendritic cell comprising one or more heterologous nucleic acid molecules, encoding for CD40L, CXCL13, and CD93.

2. A dendritic cell comprising heterologous proteins of CD40L protein, CXCL13 protein, and CD93 protein.

3. An antigen activated dendritic cell, wherein the dendritic cell comprises one or more heterologous nucleic acid molecules encoding for CD40L, CXCL13, and CD93.

4. The antigen activated dendritic cell of claim 3, wherein the one or more heterologous nucleic acid molecules encodes for CD93.

5. The antigen activated dendritic cell of claim 3, wherein the cell is activated by exposure to one or more antigens.

6. The antigen activated dendritic cell of claim 5, wherein the antigen is a tumor antigen.

7. The antigen activated dendritic cell of claim 5, wherein the antigen is a viral antigen.

8. The antigen activated dendritic cell of claim 5, wherein the antigen is a cell lysate.

9. The antigen activated dendritic cell of claim 8, wherein the cell lysate is allogeneic or autologous to the antigen activated dendritic cell.

10. The antigen activated dendritic cell of claim 8, wherein the cell lysate is a lysate comprising one, or a combination of allogeneic melanoma cell lysates.

11. The antigen activated dendritic cell of claim 8, wherein the cell lysate is a tumor cell lysate.

12. A composition of comprising a cell of claim 2, wherein the composition does not comprise a heterologous antigen.

13. A pharmaceutical composition comprising a cell of claim 2.

14. A method of treating a solid tumor, cancer, or malignancy in a subject comprising administering to the subject a cell of claim 2.

15. The method of claim 14, wherein the dendritic cell does not have the same HLA type as the subject.

16. The method claim 14, wherein the cancer is a solid tumor selected from the group consisting of fibrosarcoma, myxosarcoma, liposarcoma, chondrosarcoma, osteosarcoma, and other sarcomas, synovioma, mesothelioma, Ewing's tumor, leiomyosarcoma, rhabdomyo sarcoma, colon carcinoma/colorectal cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

17. A kit comprising a cell of claim 1, wherein the dendritic cell or composition is frozen or cryopreserved in a container, and optionally comprising a cryopreserved allogeneic tumor lysate in a separate container.

18. A kit comprising a cell of claim 8, wherein the activated dendritic cell or composition is frozen in a container.

19. A method of activating the immune system, comprising administering to a subject in need thereof an effective amount of a cell of claim 1.

20. A method of producing immature dendritic cells comprising: culturing a cell of claim 2 into immature dendritic cells in vitro.

* * * * *